US006576159B1

United States Patent
Michot et al.

(10) Patent No.: US 6,576,159 B1
(45) Date of Patent: Jun. 10, 2003

(54) MALONONITRILE-DERIVATIVE ANION SALTS, AND THEIR USES AS IONIC CONDUCTING MATERIALS

(75) Inventors: Christophe Michot, Grenoble (FR); Michel Armand, Montreal (CA); Michel Gauthier, La Prairie (CA); Yves Choquette, Sainte-Julie (CA)

(73) Assignees: Hydro-Quebec, Montreal; Centre National de la Recherche Scientifique, Paris (FR)

( * ) Notice: Subject to any disclaimer, the term of this patent is extended or adjusted under 35 U.S.C. 154(b) by 351 days.

(21) Appl. No.: 09/638,793

(22) Filed: Aug. 9, 2000

Related U.S. Application Data

(62) Division of application No. 09/101,810, filed as application No. PCT/CA97/01010 on Dec. 30, 1997, now Pat. No. 6,333,425.

(30) Foreign Application Priority Data

Dec. 30, 1996 (CA) .............................. 2194127
Mar. 5, 1997 (CA) .............................. 2199231

(51) Int. Cl.[7] .............................. H01B 1/12; H01M 6/14; H01M 10/40; C07D 233/00; C07C 255/07
(52) U.S. Cl. .............................. 252/511; 252/500; 252/510; 252/518.1; 252/519.2; 252/519.3; 252/62.2; 558/167; 558/440; 558/453; 546/256; 548/300.1; 556/1; 556/143; 429/188
(58) Field of Search .............................. 252/500, 510, 252/518.1, 519.2, 519.3; 558/167, 386, 440, 453; 546/256; 548/300.1, 340.1; 534/838; 556/1, 143

(56) References Cited

U.S. PATENT DOCUMENTS 3,793,079 A   2/1974   Brown et al.
4,851,307 A   7/1989   Armand et al.
5,072,040 A   12/1991  Armand
5,273,840 A   12/1993  Dominey
5,446,134 A   8/1995   Armand et al.
5,502,251 A   3/1996   Pohmer et al.

(List continued on next page.)

FOREIGN PATENT DOCUMENTS

| EP | 0 571 832 | 5/1993 | |
| EP | 850921 | * 1/1998 | ......... C07C/317/44 |
| WO | WO 96/24928 | 8/1996 | |
| WO | WO 96/24929 | 8/1996 | |
| WO | WO 97/23448 | 7/1997 | |
| WO | WO 97/35929 | 10/1997 | |
| WO | WO 97/35930 | 10/1997 | |
| WO | WO 98/50349 | 11/1998 | |
| WO | WO 99/49529 | 9/1999 | |
| WO | WO 00/10969 | 3/2000 | |
| WO | WO 00/11742 | 3/2000 | |

* cited by examiner

Primary Examiner—Mark Kopec
Assistant Examiner—Kallambella Vijayakumar
(74) Attorney, Agent, or Firm—Choate, Hall & Stewart

(57) ABSTRACT

The invention is related to ionic compounds, derivatives of malononitrile, in which the anionic load has been displaced. An ionic compound disclosed by the invention includes an anionic portion combined with at least one cationic portion $M^{+m}$ in sufficient number to ensure overall electronic neutrality; the compound is further comprised of M as a hydroxonium, a nitrosonium $NO^+$, an ammonium $—NH_4+$, a metallic cation with the valence m, an organic cation with the valence m, or an organometallic cation with the valence m. The anionic portion corresponds to one of the formulas $R_D—Y—C(C≡N)_2^-$ or $Z—C(C≡N)_2^-$ in which Z is an electroattractive group, $R_D$ is an organic radical, and Y is a carbonyl, a thiocarbonyl, a sulfonyl, a sulfinyl, or a phosphonyl. The compounds can be used notably for ionic conducting materials, electronic conducting materials, colorants, and the catalysis of various chemical reactions.

53 Claims, 1 Drawing Sheet

U.S. PATENT DOCUMENTS

Figure 1:
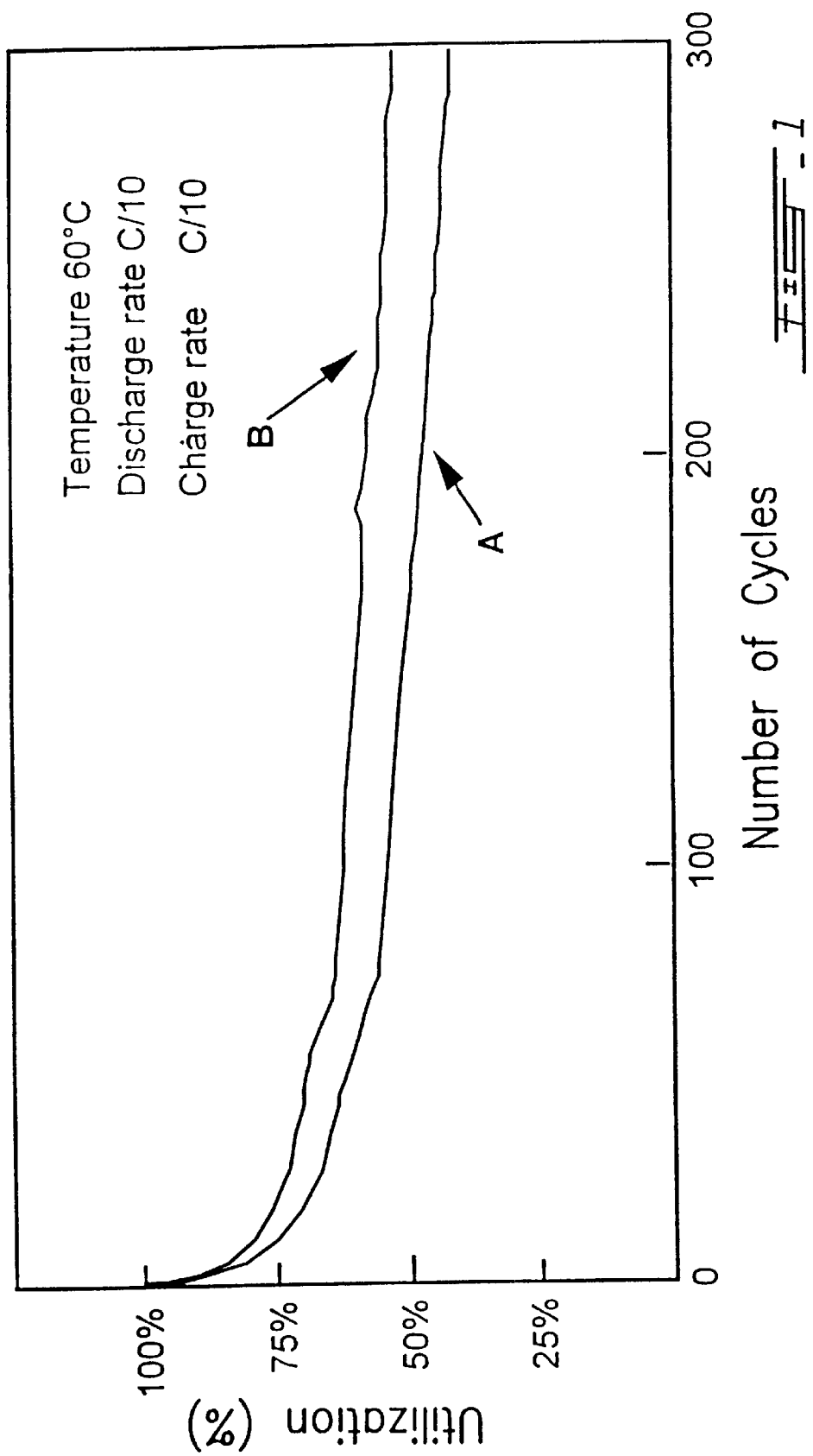

| | | |
|---|---|---|
| 5,514,493 A | 5/1996 | Waddell et al. |
| 5,609,990 A | 3/1997 | Ha et al. |
| 5,654,112 A | 8/1997 | Itou et al. |
| 5,691,081 A | 11/1997 | Krause et al. |
| 5,817,376 A | 10/1998 | Everaerts et al. |
| 5,874,616 A | 2/1999 | Howells et al. |
| 5,962,546 A | 10/1999 | Everaerts et al. |
| 6,063,522 A | 5/2000 | Hamrock et al. |
| 6,294,289 B1 * | 9/2001 | Fanta et al. ............ 429/188 |

MALONONITRILE-DERIVATIVE ANION SALTS, AND THEIR USES AS IONIC CONDUCTING MATERIALS

CROSS REFERENCE TO RELATED APPLICATIONS

This application is a divisional of U.S. patent application Ser. No. 09/101,810 filed on Nov. 19, 1998 (now U.S. Pat. No. 6,333,425), which is based on PCT Patent application No. PCT/CA97/01010 filed on Dec. 30, 1997, which is based on Canadian Patent Application No. 2,194,127 filed on Dec. 30, 1996 and on Canadian Patent Application No. 2,199,231 filed on Mar. 5, 1997.

The present invention is concerned with ionic compounds derived from malononitrile in which the anionic charge is delocalized, and their uses.

It is known and particularly interesting to introduce ionic groups in organic molecules or polymers having various functions. Coulombic forces correspond, indeed, to the stronger interactions which are available at the molecular level, and the ionic groups modify in a very noted manner the molecules to which they are attached. Coloring materials which are made soluble in water by means of sulfonate or carboxylate functions may be mentioned.

However, the —$CO_2^-$1/m$M^{m+}$ or —$SO_3^-$1/m$M^{m+}$ groups of this type are not dissociated, and they cause no solubility in solvents except water or certain highly polar protic solvents such as light alcohols, which considerably restrict the scope of their use.

On the other hand, salts of the compounds [$R_FSO_2$—N—$SO_2R_F$]$^-$1/m$M^{m+}$ in which $R_F$ is a perfluorinated group and $M^{m+}$ is a cation of valence m+ which are soluble and are dissociated in ordinary aprotic media or solvating polymers, are known. It is however considered that the existence of two perfluoroalkylsulfonyl groups (in particular the existence of fluorine atoms on the a atom of carbon of each sulfonyl group) which exert an important attracting power on the electrons of the anionic charge, is a necessary condition to obtain properties of solubility and dissociation. For example, the $pK_a$ of the acid H[$CF_3SO_2$—N—$SO_2CF_3$] is only 1.95, as compared to that of the non-fluorinated acid $CH_3SO_3H$ ($pK_a$=0.3) and is clearly inferior to that of the perfluorinated acid $CF_3SO_3H$ ($pK_a$<−9) because of the basic character of the central nitrogen atom.

Surprisingly, the inventors have found that the compounds containing ionic groups —$C(CN)_2^-$ have excellent properties of solubility and dissociation, even when they contain no highly electroattractive perfluorinated groups.

The present invention consequently aims at supplying a family of ionic compounds having a good solubility and a good dissociation, without requiring complex modifications of the starting molecule. The precursors of the molecules of the invention are for the most part industrial products and/or easily accessible. In addition, it should be noted that the absence, or at least the decrease of the perfluorinated fraction in the compounds of the invention, enables to reduce production costs of the compounds and consequently the cost of the resulting applications.

An object of the present invention is an ionic compound which is a derivative of malononitrile comprising an anionic part which is associated to at least one cationic part $M^{+m}$ in a sufficient number to provide for the electronic neutrality of the whole, characterized in that M is a hydroxonium, a nitrosonium $NO^+$, an ammonium —$NH_4^+$, a metallic cation having a valency m, an organic cation having a valency m or an organometallic cation having a valency m, and in that the ionic part corresponds to one of the formulae $R_D$—Y—$C(C\equiv N)_2^-$ or Z—$C(C\equiv N)_2^-$ in which:

Z represents an electroattractor radical having a Hammett parameter at least equal to that of a phenyl radical, selected from:

j) —CN, —$NO_2$, —SCN, —$N_3$, $FSO_2$—, —$CF_3$, $R'_FCH_2$— ($R'_F$ being a perfluorinated radical, preferably $CF_3$—), fluoroalkyloxy, fluoroalkylthioxy, fluoroalkenyloxy, fluoroalkenylthioxy radicals;

jj) radicals comprising one or more aromatic nuclei possibly containing at least one nitrogen, oxygen, sulfur or phosphorus atom, said nuclei possibly being condensed nuclei and/or said nuclei possibly carrying at least one substituent selected from halogens, —CN, —$NO_2$, —SCN, —$N_3$, $CF_2$=CF—O—, radicals $R_F$— and $R_FCH_2$— in which $R_F$ is a perfluoroalkyl alkyl having 1 to 12 carbon atoms, fluoroalkyloxy groups, fluoroalkylthioxy groups, alkyl, alkenyl, oxa-alkyl, oxa-alkenyl, aza-alkyl, aza-alkenyl, thia-alkyl, thia-alkenyl radicals, polymer radicals, radicals having at least one cationic ionophorous group and/or at least one anionic ionophorous group;

with the proviso that one substituent Z may be a monovalent radical, a multivalent radical, or part of a multivalent radical (including a dendrimer) carrying at least one group —$C(C\equiv N)_2$, or a segment of a polymer;

Y represents a carbonyl group, a thiocarbonyl group, a sulfonyl group, a sulfinyl group or a phosphonyl group and:

$R_D$ is a radical selected from:

a) alkyl or alkenyl radicals, aryl, arylalkyl, alkylaryl or alkenylaryl radicals, alicyclic or heterocyclic radicals, including polycyclic radicals;

b) alkyl or alkenyl radicals comprising at least one functional ether, thioether, amine, imine, amide, carboxyl, carbonyl, isocyanate, isothiocyanate, hydroxy;

c) aryl, arylalkyl, arylalkenyl, alkylaryl or alkenylaryl radicals, in which the aromatic nuclei and/or at least one substituent of the nucleus comprises heteroatoms such as nitrogen, oxygen, sulfur;

d) radicals comprising condensed aromatic cycles which possibly comprise at least one heteroatom selected from nitrogen, oxygen, sulfur;

e) halogenated or perhalogenated alkyl, alkenyl, aryl, arylalkyl, alkylaryl radicals, said radicals possibly comprising functional ether, thioether, imine, amine, carboxyl, carbonyl or hydroxy groups;

f) radicals $R_CC(R')(R'')$—O— in which $R_C$ is an alkyl perfluorinated radical and R' et R" are independently from one another a hydrogen atom or a radical such as defined in a), b), c) or d) above [for example $CF_3CH_2O$—, $(CF_3)_3CO$—, $(CF_3)_2CHO$—, $CF_3CH(C_6H_5)O$—, —$CH_2(CF_2)_2CH_2$—];

g) radicals $(R_B)_2N$—, in which the radicals $R_B$ which are identical or different are such as defined in a), b), c), d) and e) above, one of the $R_B$ may be a halogen atom, or the two radicals $R_B$ together form a divalent radical which constitutes a cycle with N;

h) polymer radicals;

i) radicals having one or more cationic ionophorous groups and/or one or more anionic ionophorous groups;

with the proviso that one substituent $R_D$ may be a monovalent radical, part of a multivalent radical carrying a plurality of —Y—C⁻(C≡N)₂ groups or a segment of a polymer;

with the proviso that when Y is a carbonyl and $R_D$ is a perfluoroalkyl radical having 1 to 3 carbon atoms, or when Z is —CN, M is different from an alkali metal.

According to an embodiment of the invention, the cation is a metallic cation selected from cations of alkali metals, cations of alkali-earth metals, cations of transition metals, cations of trivalent metals, cations of rare earths. By way of example, $Na^+$, $Li^+$, $K^+$, $Sm^{3+}$, $La^{3+}$, $Ho^{3+}$, $Sc^{3+}$, $Al^{3+}$, $Y^{3+}$, $Yb^{3+}$, $Lu^{3+}$, $Eu^{3+}$, may be mentioned.

The cation may also be an organometallic cation, such as a metallocenium. By way of example, the cations derived from ferrocene, titanocene, zirconocene, from an indenocenium or a metallocenium arene, cations of transition metals complexed with ligands of phosphine type possibly having a chirality, organometallic cations having one or more alkyl or aryl groups covalently fixed to an atom or a group of atoms, may be mentioned. Specific examples include methylzinc, phenylmercury, trialkyltin or trialkyllead, chloro[ethylene-bis(indenyl)] zirconium (IV) or tetrakis-(acetonitrile)palladium(II). The organo-metallic cation may be part of a polymer chain.

In a specific embodiment of the invention, the organic cation is an onium cation selected from the group consisting of $R_3O^+$(oxonium), $NR_4^+$(ammonium), $RC(NHR_2)_2^+$ (amidinium), $C(NHR_2)_3^+$(guanidinium), $C_5R_6N^+$ (pyridinium), $C_3R_5N_2^+$(imidazolium), $C_3R_7N_2^+$ (imidazolinium), $C_2R_4N_3^+$(triazolium), $SR_3^+$(sulfonium), $PR_4^+$(phosphonium), $IR_2^+$(iodonium), $(C_6R_5)_3C^+$ (carbonium) cations. In a given onium cation, the radicals R may all be similar. However, an onium cation may also include radicals R which are different from one another. A radical R may be a H or it may be selected from the following radicals:

alkyl, alkenyl, oxa-alkyl, oxa-alkenyl, aza-alkyl, aza-alkenyl, thia-alkyl, thia-alkenyl, aryl, arylalkyl, alkylaryl, alkenylaryl radicals, dialkylamino radicals and dialkylazo radicals;

cyclic or heterocyclic radicals possibly comprising at least one lateral chain comprising heteroatoms such as nitrogen, oxygen, sulfur;

cyclic or heterocyclic radicals possibly comprising heteroatoms in the aromatic nucleus;

groups comprising a plurality of aromatic or heterocyclic nuclei, condensed or non-condensed, possibly containing at least one nitrogen, oxygen, sulfur or phosphorus atom.

When an onium cation carries at least two radicals R which are different from H, these radicals may together form a cycle which is aromatic or non-aromatic, possibly enclosing the center carrying the cationic charge.

When the cationic part of a compound of the invention is an onium cation, it may be either in the form of an independent cationic group which is bound to the cationic part only by the ionic bond between the positive charge of the cation and the negative charge of the anionic part. In this case, the cationic part may be part of a recurring unit of a polymer.

An onium cation may also be part of the radical Z or the radical $R_D$ carried by the anionic center. In this case, a compound of the invention constitutes a zwitterion. When the cation of a compound of the invention is an onium cation, it may be selected so as to introduce in the compound substituents enabling to give specific properties to said compound. For example, the cation $M^+$ may be a cationic heterocycle with aromatic character, including at least one alkylated nitrogen atom in the cycle. By way of example, an imidazolium, a triazolium, a pyridinium, a 4-dimethyl-amino-pyridinium may be mentioned, said cations possibly carrying a substituent on the carbon atoms of the cycle. Among these cations, those in which the salts have a melting point lower than 150° C., more particularly lower than 25° C.

A compound of the invention in which the cation M is a group carrying a diazoic group having —N=N—, —N=N⁺, a sulfonium group, an iodonium group, a phosphonium group or a substituted or non-substituted arene-ferrocenium cation, possibly incorporated in the polymeric network, is interesting inasmuch as it is activatable by a source of actinic energy of suitable wavelength. Specific examples of such compounds include those in which the cation is a diaryliodonium cation, a dialkylaryliodonium cation, a triarylsulfonium cation, a trialkylaryl sulfonium cation, or a substituted or non-substituted phenacyl-dialkyl sulfonium cation. The above cations may be part of a polymer chain.

The cation M of a compound of the invention may be an organic cation incorporating a group 2,2'[azobis(2-2'-imidazolinio-2-yl)propane]²⁺ or 2,2'-azobis(2-amidiniopropane)²⁺. The compound the invention is then particularly interesting as a free radical initiator, which is thermally activatable and non-volatile, soluble in polar organic solvents and in aprotic solvating monomers and polymers.

A specific family of compounds of the invention is the one which comprises a group $R_DY$—. The compounds in which Y is —$SO_2$— or —CO— are especially preferred.

The choice of substituent $R_D$ enables to adjust the properties of a compound of the invention. In an embodiment, $R_D$ is selected from alkyl, alkenyl, oxa-alkyl, oxa-alkenyl, aza-alkyl, aza-alkenyl, thia-alkyl or thia-alkenyl having 1 to 24 carbon atoms, or from aryl, arylalkyl, alkylaryl or alkenylaryl radicals having 5 to 24 carbon atoms.

According to another embodiment, $R_D$ is selected from alkyl or alkenyl radicals having 1 to 12 carbon atoms and possibly comprising at least one heteroatom O, N or S in the main chain or in a lateral chain, and/or possibly carrying a hydroxy group, a carbonyl group, an amine group or a carboxyl group.

According to another embodiment, $R_D$ is selected from aryl, arylalkyl, alkylaryl or alkenylaryl radicals, in which the aromatic nuclei and/or their substituents comprise heteroatoms such as nitrogen, oxygen, sulfur.

Substituent $R_D$ may be a polymer radical, for example a poly(oxyalkylene) radical. A compound of the invention is then in the form of a polymer carrying an ionic group —Y—C(CN)₂⁻, $M^+$.

$R_D$ may be a recurring unit of a polymer, for example an oxyalkylene unit or a styrene unit. The compound of the invention is then in the form of a polymer in which at least part of the recurring units carry a lateral group on which an ionic group —Y—C(CN)₂⁻, $M^+$ is fixed. By way of example, there may be mentioned a poly(oxyalkylene) in which at least certain oxyalkylene units carry a substituent —Y—C(CN)₂⁻, $M^+$ or a polystyrene in which at least certain styrene units carry a substituent —Y—C(CN)₂⁻, $M^+$.

A particular category of compounds according to the invention comprises the compounds in which substituent $R_D$ has at least one anionic ionophorous group and/or at least one cationic ionophorous group. The anionic group may for example be a carboxylate function (—CO₂⁻), a sulfonate function (—SO₃⁻), a sulfonimide function (—SO₂NSO₂—)

or a sulfonamide function (—SO$_2$N—). The ionophorous group may for example be an iodonium, sulfonium, oxonium, ammonium, amidinium, guanidinium, pyridinium, imidazolium, imidazolinium, triazolium, phosphonium or carbonium group. The cationic ionophorous group may act totally or partially as a cation M.

When R$_D$ includes at least one ethylenic unsaturation and/or a condensable group and/or a dissociable group by thermal means, by photochemical means or by ionic dissociation, the compounds of the invention are reactive compounds which may be subject to polymerizations, crosslinkings or condensations, possibly with other monomers. They may also be used to fix ionophorous groups on the polymers carrying a suitable reactive function.

A substituent R$_D$ may be a mesomorphous group or a chromophore group or a self-doped electronically conductive polymer or a hydrolyzable alkoxysilane.

A substituent R$_D$ may include a group capable of trapping free radicals, for example a hindered phenol or a quinone.

A substituent R$_D$ may also include a dissociating dipole, for example an amide function, a sulfonamide function or a nitrile function.

A substituent R$_D$ may also include a redox couple, a disulfide group, a thioamide group, a ferrocene group, a phenothiazine group, a bis(dialkylaminoaryl) group, a nitroxide group or an aromatic imine group.

A substituent R$_D$ may also include a complexing ligand, or an optically active group.

Another category of compounds of the invention comprises compounds in which Y is a carbonyl group, R$_D$—CO— representing an amino acid, or an optically or biologically active polypeptide.

According to another variant, a compound according to the invention comprises a substituent R$_D$ which represents a radical having a valency v higher than 2, itself including at least one group —Y—C(CN)$_2$$^-$, M$^+$. In this case, the negative charges which are present on the anionic part of the compound of the invention should be compensated by the appropriate number of cations or cationic ionophorous groups M.

When a compound of the present invention corresponds to the formula Z—C(CN)$_2$$^-$, M$^+$ in which Z is an electroattractor group which is not bonded to the nitrogen atom carrying the negative charge by means of a group —SO$_x$—, Z is advantageously selected from the group consisting of —OC$_n$F$_{2n+1}$, —OC$_2$F$_4$H, —SC$_n$F$_{2n+1}$ and —SC$_2$F$_4$H, —OCF=CF$_2$, —SCF=CF$_2$, n being a whole number from 1 to 8. Z may also be a radical C$_n$F$_{2n+1}$CH$_2$—, n being a whole number from 1 to 8.

The compounds of the invention may be obtained by a process in which a compound R$_D$—Y—L or Z—L is reacted with a compound [A—C(CN)$_2$]$^{n-}{}_m$nM$^{\prime m+}$, Z and R$_D$ being such as defined previously, M' being H or a cation such as defined previously for M, L represents an electronegative starting group such as a halogen, a N-imidazoyl radical, a N-triazoyl radical, a compound giving an activated ester (for example a succinimidyloxy, a benzotriazoloxy or a O-acylurea), an alkoxide group, a R$_D$—Y—O— group or a R$_D$—Y—S— group, and A represents a cation M$^{\prime m+}$, a trialkylsilyl group, a trialkyl germanyl group, a trialkylstannyl group or a tertioalkyl group, in which the alkyl substituents have 1 to 6 carbon atoms.

By way of example, there should be mentioned the reaction of a flurosulfonyl fluoride with a di-salt of malononitrile according to the following reaction scheme:

FSO$_2$—F+[NaC(CN)$_2$]$^-$Na$^+$→NaF+[FSO$_2$—C(CN)$_2$]$^-$Na$^+$.

The use of a compound [A—C(CN)$_2$]$^{n-}{}_m$nM$^{\prime m+}$ in which A is a tertioalkyl group is advantageous, since such a group is a proton precursor by formation of the corresponding alkene. The use of the trialkylsilyl group is especially interesting when the starting group is a fluorine, due to the very high stability of the bond F—Si.

When a compound [A—C(CN)$_2$]$^{n-}{}_m$nM$^{\prime m+}$ in which A is the proton is used, it is advantageous to carry out the reaction in the presence of a tertiary base or a congested base T capable of forming the salt L$^-$(HT$^+$) by combination with the proton, in order to promote the formation of the compound of the invention. The base may be selected among alkylamides (for example triethylamine, di-isopropylamine, quinuclidine), 1,4-diazobicyclo[2,2,2]octane (DABCO); pyridines (for example pyridine, alkylpyridines, dialkylaminopyridines); imidazoles (for example N-alkylimidazoles, imidazo[1,1-a]pyridine); amidines (for example 1,5-diazabicyclo[4,3,0]non-5-ene (DBN), 1,8-diazabicyclo[5,4,0]undec-7-ene (DBU)); guanidines (for example tetramethyl guanidine, 1,3,4,7,8-hexahydro-1-methyl-2H-pyrimido[1,2-a]pyrimidine (HPP). An alkali metal salt of malononitrile can also be used as a base.

By way of example of such a process, the process in which a carbonyl chloride R$_D$COCl is reacted with malononitrile in the presence of DABCO may be mentioned.

A compound of the invention may also be obtained by direct coupling between a malononitrile salt and a carboxylic acid by means of a coupling agent. When Z=CO, it is advantageous to use a compound RZX of the type pseudohalide directly prepared in-situ (X=RCO$_2$, SCO, PTO, BzO . . . ) from RCOOH by action of the condensation agents used in the synthesis of peptides (molecular dehydrating agents). Such agents are described for example in *Synthesis* p. 453 (1972) and in *Ann. Rev. Biochem* 39, 841 (1970). The compounds of the invention are then prepared from RCOOH to which the molecular dehydration agent is added, and also the compound (1/nM)[(NC)$_2$CH] in stoichiometric proportions in a polar solvent. Preferably, the condensation agent is selected from carbodiimides, for example cyclohexyl carbodiimide or diisopropyl carbodiimide; carbonates and oxalates of succinimidyl, phthalimidyl, benzotriazolyl, of nitro-, dinitro- or perhalo-phenols, of trifluoroethyl, of trichloroethyl; the mixture Pφ$_3$-diethylazodicarboxylate (DEAD) or Pφ$_3$-dithiodipyridine; carbonyldiimidazole (Im)$_2$CO or phenylphosphorodiimidazole φPO(Im)$_2$; amide acetals, for example dimethylformamide di-neopentyl acetal (CH$_3$)$_2$NCH[OCH$_2$C(CH$_2$)$_2$]$_2$; 2-alcoxy-1-alkoxycarbonyl-1,2-dihydroquinoline; salts of O-benzo triazol-1-yl-N,N,N',N'-tetramethyluronium or O-benzo triazol-1-yloxytrisdimethylaminophosphonium; aromatic sultones, for example 2,2-(6-nitronaphth[1,8-cd]-1,2-oxathiazoyl) oxide, iosbutyl chloroformate, diphenylphosphochloroiridate, ethylene chlorophosphite, diethylethylene pyrophosphite, bis(2-oxo-3-oxazolidinyl) phosphinyl chloride; 2-ter-butyl-5-methyl isooxazolium salts (Woodward's reagent L).

The cation of the compound obtained according to either of the processes described above may be replaced by the known processes of cationic exchange, either by precipitation or selective extractions, or by the use of ion exchange resins.

In addition, the substituent R$_D$ of a compound of the invention may be modified by known reactions. For example, a substituent R$_D$ which comprises an allyl group maybe converted by reaction with a peroxide to give an expoxidized substituent R$_D$. A group —NHR may be converted into a vinylester group by reaction with potassium tert-butoxide and vinylchloroformate. Processes to carry out these modifications and others are available to one skilled in the art.

The ionic compounds of the present invention comprise at least one ionophorous group on which substituents of highly various natures are fixed. Bearing in mind the large possible choice for the substituents, the compounds of the invention enable to provide properties of ionic conduction in most organic, liquid or polymer medias having even a low polarity. The applications are important in the field of electrochemistry, in particular for storing energy in primary or secondary generators, in supercapacitances, in combustible batteries and in electroluminescent diodes. The compatibility of the ionic compounds of the invention with polymers or organic liquids enables to provide noted antistatic properties, even when the amount of ionic compound is extremely low. The compounds of the invention which are polymers, as well as polymeric compounds obtained from the compounds of the invention having the property of polymerizing or copolymerizing, have the properties listed above with the advantage of having an unmovable anionic charge. This is why another object of the present invention consists of an ionically conductive material made of an ionic compound of the present invention in solution in a solvent.

According to an embodiment, the ionic compound used for preparing an ionically conductive material is selected from compounds in which the cation is ammonium, or a cation derived from a metal, in particular lithium or potassium, zinc, calcium, rare earth metals, or an organic cation, such as a substituted ammonium, an imidazolium, a triazolium, a pyridinium, a 4-dimethylamino-pyridinium, said cations possibly carrying a substituent on the carbon atoms of the cycle. The ionically conductive material thus obtained has a high conductivity and solubility in solvents, due to the low interactions between the positive charge and the negative charge. Its range of electrochemical stability is wide, and it is stable in reducing as well as oxidizing media. Moreover, the compounds which have an organic cation and a melting point lower than 150° C., in particular compounds of imidazolium, triazolium, pyridinium, 4-dimethylamino-pyridinium have a high intrinsic conductivity, even in the absence of solvents when they are in molten phase.

The properties of the ionically conductive material may also be modified by the choice of substituent Y or $R_D$.

The choice of an alkyl group, an aryl group, an alkylaryl group or an arylalkyl group for $R_D$ enable to provide in the ionically conductive material properties of the type mesogene, in particular alkyl groups containing 6 to 20 carbon atoms, arylalkyl groups, in particular both containing the biphenyl entity which form phases of the liquid crystal type. Properties of conduction in phases of the liquid crystal, nematic, cholesteric or discotic type are interesting for applications concerning optical postings or for reducing the mobility of anions in electrolytes, in particular in polymer electrolytes, without affecting the mobility of the cations. This characteristic is important for applications in electrochemical generators, in particular those utilizing lithium cations.

When the substituent $R_D$ contains mesomorphous group or a group to comprising at least one ethylenic unsaturation and/or a condensable group and/or a group which is dissociable by thermal means, by photochemical means or by ionic dissociation, the ionically conductive material easily forms polymers or copolymers which are polyelectrolytes, the latter being intrinsically polyelectrolytes when the polymer carries solvating groups, or becomes polyelectrolytes by addition of a is polar solvent of the liquid or polymer type, or by mixture with such a solvent. These products have a conductivity which is solely due to the cations, which constitutes a property which is very useful in applications of the electrochemical generator type. In low molar fraction in a copolymer, they give rise to stable antistatic properties which are hardly dependent on humidity and cause the fixation of cationic colorants, this property being useful for textile fibers and lasers with coloring materials.

The presence of a substituent $R_D$ which is a self-doped electronically conductive polymer improves the stability of the ionically conductive material with respect to outside agents. The conductivity is stable in time even at high temperatures. In contact with metals, these materials give very low interface resistances and protect in particular ferrous metal or aluminum from corrosion.

When the substituent $R_D$ is a hydrolyzable alkoxysilane, the ionically conductive material may form stable polymers by a simple mechanism of hydrolysis-condensation in the presence of water, thus enabling to treat surfaces of oxides, of silica, of silicates, in particular glass, to induce properties of surface conduction, antistatic properties, or to promote the adhesion of polar polymers.

When the substituent $R_D$ is a group comprising a free radical trap such as a hindered phenol, or a quinone, the ionically conductive material has the following advantages and properties: it acts as an antioxidant having no volatility and being compatible with polar monomers and polymers, to which it also gives antistatic properties.

When the substituent $R_D$ comprises a dissociating dipole such as an amide, a sulfonamide or a nitrile, the ionically conductive material has an improved conductivity in media of low or medium polarity, in particular in solvating polymers, which enables to minimize, even to prevent the addition of solvents or of volatile plasticizing agents.

The presence of a substituent $R_D$ which contains a redox couple such as a disulfide, a thioamide, a ferrocene, a pheno-thiazine, a bis(dialkylaminoaryl) group, a nitroxide, an aromatic imide, enables to induce in the ionically conductive material properties of redox shuttle useful as protective elements and charge equalization of electrochemical generators, in photoelectrochemical systems, in particular in systems of conversion of light into electricity, in systems of modulation of light of the electrochrome type.

The presence of a substituent $R_D$ which is a complexing ligand in an ionically conductive material enables to chelate metallic cations, in particular those which have an elevated charge (2, 3 and 4), in the form of soluble complex in organic media, including in aprotic media, and enables the transport of these cations in particular in the form of anionic complex, in solvating polymers. The metallic cations of elevated charge are indeed immovable in solvating polymers. This type of complexing agents gives with certain cations of transition metals (Fe, Co . . . ) or certain rare earths (Ce, Eu . . . ) redox couples which are particularly stable. ionically conductive materials containing a compound of the invention in which $R_D$ is an alkyl or alkenyl substituent which contains at least one heteroatom selected from O, N and S have a complexing and plasticizing capacity, in particular in polar polymers and especially polyethers. The heteroatoms N and S are selectively complexing for cations of transition metals Zn and Pb.

When an alkyl or alkenyl substituent $R_D$ additionally carries a hydroxy group, a carbonyl group, an amine group, a carboxyl group, the ionic compound of the invention may give by polycondensation a polymer or a copolymer and the ionically conductive material which contains such a polymer or copolymer have polyelectrolytic properties.

The presence, in a ionically conductive material of the invention, of a compound in which $R_D$ is selected from aryl, arylalkyl, alkylaryl or alkenylaryl radicals, in which the lateral chains and/or the aromatic nuclei comprise heteroatoms such as nitrogen, oxygen, sulfur, improves dissociation and increases the possibility of producing complexes depending on the position of the heteroatom (pyridine) or of giving by duplicative oxidation conjugated polymers or copolymers (pyrrol, thiophene).

When the ionically conductive material contains a compound of the invention in which $R_D$ represents a recurring unit of a polymer chain, the material constitutes a polyelectrolyte.

A compound of the invention in which the substituent Z is selected from the group consisting of $-OC_nF_{2n+1}$, $-OC_2F_4H$, $-SC_nF_{2n+1}$ and $-SC_2F_4H$, $-OCF=CF_2$, $-SCF=CF_2$, n being a whole number from 1 to 8, is a precursor of stable monomers and polymers, in particular towards oxygen even at elevated temperatures of 80° C. when dealing with polymers. An ionically conductive material which contains such a compound is therefore particularly appropriate as an electrolyte of a combustible battery.

An ionically conductive material of the present invention comprises an ionic compound of the invention in solution in a solvent.

The solvent may be an aprotic liquid solvent, a polar polymer or one of their mixtures.

The aprotic liquid solvent is selected for example from linear ethers and cyclic ethers, esters, nitriles, nitro derivatives, amides, sulfones, sulfolanes, alkylsulfamides and partially hydrogenated hydrocarbons. The solvents which are particularly preferred are diethylether, dimethoxyethane, glyme, tetrahydrofurane, dioxane, dimethyltetrahydrofurane, methyl or ethyl formate, propylene or ethylene carbonate, alkyl carbonates (such as dimethylcarbonate, diethylcarbonate and methylpropylcarbonate), butyrolactones, acetonitrile, benzonitrile, nitromethane, nitrobenzene, dimethylformamide, diethylformamide, N-methylpyrrolidone, dimethylsulfone, tetramethylene sulfone, tetramethylene sulfone and tetraalkylsulfonamides having 5 to 10 carbon atoms.

An ionically conductive material of the present invention may simultaneously comprise an aprotic liquid solvent selected from the aprotic liquid solvents mentioned above and a polar polymer solvent comprising units containing at least one heteroatom selected from sulfur, nitrogen, oxygen and fluorine. It may comprise from 2 to 98% liquid solvent. By way of example of such a polar polymer, polymers which mainly contain units derived from acrylonitrile, vinylidene fluoride, N-vinylpyrrolidone or methylmethacrylate may be mentioned. The proportion of aprotic liquid in the solvent may vary from 2% (corresponding to a plasticized solvent) to 98% (corresponding to a gelled solvent).

An ionically conductive material of the present invention may additionally contain a salt commonly used in the prior art to prepare an ionically conductive material. Among the salts which may be used in admixture with an ionic compound of the invention, a salt selected from perfluoroalcanesulfonates, bis(perfluoroalkylsulfonyl) imides, bis(perfluoroalkylsulfonyl) methanes and tris (perfluoroalkylsulfonyl) methanes are particularly preferred.

Of course, an ionically conductive material of the invention may additionally contain additives normally used in this type of material, such as mineral or organic charges in the form of a powder or fibers.

An ionically conductive material of the invention may be used as electrolyte in an electrochemical general. The present invention thus has as an object an electrochemical generator comprising a negative electrode and a positive electrode separated by an electrolyte, characterized in that the electrolyte is an ionically conductive material as defined above. According to a particular embodiment, such a generator comprises a negative electrode consisting of metallic lithium, or an alloy thereof, possibly in the form of a nanometric dispersion in lithium oxide, or a double nitride of lithium and a transition metal, or a low potential oxide having the general formula $Li_{1+y+x/3}Ti_{2-x/3}O_4$ ($0 \leq x \leq 1$, $0 \leq y \leq 1$), or carbon and the carbonated products resulting from the pyrolysis of organic materials. According to another embodiment, the generator comprises a positive electrode selected from vanadium oxides $VO_x$ ($2 \leq x \leq 2,5$), $LiV_3O_8$, $Li_yNi_{1-x}Co_xO_2$, ($0 \leq x \leq 1$; $0 \leq y \leq 1$), manganese spinels $Li_yMn_{1-x}M_xO_2$ (M=Cr, Al, V, Ni, $0 \leq x \leq 0,5$; $0 \leq y \leq 2$), organic polydisulfides, FeS, $FeS_2$, iron sulfate $Fe_2(SO_4)_3$, iron and lithium phosphates and phosphosilicates of olivine structure, or substituted products wherein iron is substituted by manganese, used alone or in admixtures. The collector of the positive is preferably made of aluminum.

An ionically conductive material of the present invention may also be used in a supercapacitance. Another object of the present invention is consequently to provide a supercapacitance utilizing at least one carbon electrode of high specific surface, or an electrode containing a redox polymer, in which the electrolyte is an ionically conductive material as defined above.

An ionically conductive material of the present invention may also be used for the p or n doping of an electronically conductive material and this use constitutes another object of the present invention.

In addition, an ionically conductive material of the present invention may be used as an electrolyte in an electrochrome device. An electrochrome device in which the electrolyte is an ionically conductive material according to the invention is another object of the present invention.

It was observed that the strong dissociation of ionic species of compounds of the invention results in a stabilization of carbocations, in particular those in which there is a conjugation with oxygen and nitrogen and, surprisingly, in a strong activity of the proton form of the compounds of the invention on certain monomers. The present invention therefore also has as an object the use of the ionic compounds as photoinitiators which constitute sources of Brønsted acids, which are catalysts for the polymerization or cross-linking of monomers or polymers capable of cationic reaction, or as catalysts for the modification of polymers.

The process of polymerization or cross-linking of monomers or prepolymers capable of cationic reaction is characterized in that there is used a compound of the invention as photoinitiator constituting a source of acid catalyzing the polymerization reaction. The compounds according to the invention in which the cation is a group having a bond $-N=N^+$, $-N=N-$, a sulfonium group, an iodonium group, or an arene-ferrocenium cation which is substituted or non-substituted, possibly incorporated in a polymeric network, are particularly preferred.

The choice of substituent $R_D$ or substituent Z is made so as to increase the solubility of said compound in the solvents used for the reaction of monomers or prepolymers, and as a function of the desired properties for the final polymer. For example, the choice of non-substituted alkyl radicals gives a solubility in low polar media. The choice of radicals comprising an oxa group or a sulfone will give a solubility in polar media. The radicals including a sulfoxide group, a sulfone group, a phosphine oxide group, a phosphonate group, respectively obtained by the addition of oxygen on the atoms of sulfur or phosphorus, may give to the polymer obtained improved properties with respect to adhesion, shine, resistance to oxidation or to UV. The monomers and prepolymers which may be polymerized or cross-linked with the photoinitiators of the present invention are those which may undergo a cationic polymerization.

The monomers and prepolymers which may be polymerized or cross-linked with the photoinitiators of the present invention are those which may be subject to cationic polymerization.

Among the monomers, monomers which include a cyclic ether function, a cyclic thioether function or cyclic amine function vinyl compounds (more particularly vinyl ethers), oxazolines, lactones and lactames may be mentioned.

Among the polymers of the ether or cyclic thioether type, ethylene oxide, propylene oxide, oxetane, epichlorhydrin, tetrahydrofurane, styrene oxide, cyclohexene oxide, vinylcyclohexene oxide, glycidol, butylene oxide, octylene oxide, glycidyl ethers and esters (for example glycidyl methacrylate or acrylate, phenyl glycidyl ether, diglycidylether of bisphenol A or its fluorinated derivatives), cyclic acetals having 4 to 15 carbon atoms (for example dioxolane, 1,3-dioxane, 1,3-dioxepane) and spiro-bicyclo dioxolanes may be mentioned.

Among vinyl compounds, vinyl ethers constitute a very important family of monomers which are capable of cationic polymerization. By way of example, there may be mentioned ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimethanol monovinyl ether, cyclohexanedimethanol divinyl ether, 2-ethylhexyl vinyl ether, poly-THF-divinyl ether having a molecular weight between 150 and 5,000, diethyleneglycol monovinyl ether, trimethylolpropane trivinyl ether, aminopropyl vinyl ether, 2-diethylaminoethyl vinyl ether.

Other vinyl compounds may include, by way of example, 1,1-dialkylethylenes (for example isobutene), vinyl aromatic monomers (for example styrene, α-alkylstyrenes, such as α-methylstyrene, 4-vinylanisole, acenaphthene) N-vinyl compounds (for examples N-vinylpyrolidone or N-vinyl sulfonamides).

Among prepolymers, there may be mentioned compounds in which epoxy groups are carried by an aliphatic chain, an aromatic chain, or a heterocyclic chain, for example glycidicethers of bisphenol A which are ethoxylated by 3 to 15 ethylene oxide units, siloxanes having lateral groups of the epoxycyclohexene-ethyl type obtained by hydrosilylation of copolymers of dialkyl, alkylaryl or diaryl siloxane with methyl hydrogenosiloxane in the presence of vinylcyclohexene oxide, condensation products of the sol-gel type obtained from triethoxy or trimethoxy silapropylcyclohexene oxide, urethanes incorporating the reaction products of butanediol monovinylether and an alcohol of a functionality higher than or equal to 2 with an aliphatic or aromatic di- or tri-isocyanate.

The process of polymerization according to the invention consists in mixing at least one monomer or prepolymer capable of cationic polymerization and at least one ionic compound of the invention, and subjecting the mixture obtained to actinic or β radiation. Preferably, the reaction mixture is subjected to radiation having been formed into a thin layer having a thickness lower than 5 mm, preferably in the form of a thin layer having a thickness lower than or equal to 500 μm. The duration of the reaction depends on the thickness of the sample and the power of the source at the active λ wavelength. It is defined by the speed at which it passes in front of the source, which is between 300 mm/min and 1 cm/min. Layers of the final material having a thickness greater than 5 mm may be obtained by repeating many times the operation consisting in spreading a layer and treating it with the radiation.

Generally, the quantity of photoinitiator used is between 0.01 and 15% by weight with respect to the weight of the monomer or prepolymer, preferably between 0.1 and 5% by weight.

An ionic compounds of the present invention may be used as photoinitiator in the absence of solvent, for example when it is intended to polymerize liquid monomers in which the ionic compound used as photoinitiator is soluble or easily dispersible. This type of utilization is particularly interesting, since it enables to overcome the problems associated with solvents (toxicity, flammability).

An ionic compound of the present invention may also be used as photoinitiator in the form of a homogeneous solution in a solvent which is inert towards polymerization, ready to be used and easily dispersible, in particular in the case where the medium to be polymerized or cross-linked has a high viscosity.

As example of an inert solvent, there may be mentioned volatile solvents, such as acetone, methyl-ethyl ketone and acetonitrile. These solvents will be used simply to dilute the products to be polymerized or cross-linked (to make them less viscous, especially when dealing with a prepolymer). They will be removed by drying after polymerization or cross-linking. Non-volatile solvents may also be mentioned. A non-volatile solvent also serves to dilute the products that one wishes to polymerize or cross-link, and to dissolve the ionic compound of the invention used as photoinitiator, however, it will remain in the material formed and will thus act as plasticizing agent. By way of example, propylene carbonate, γ-butyrolactone, ether-esters of mono-, di-, tri-ethylene or propylene glycols, ether-alcohols of mono-, di-, tri-ethylene or propylene glycols, plasticizing agents such as esters of phthalic acid or citric acid, may be mentioned.

According to another embodiment of the invention, there may be used as solvent or diluent a compound which is reactive towards polymerization, which is a compound of low molecular weight and of low viscosity which will simultaneously act as polymerization monomer and solvent or diluent for more viscous polymers or prepolymers used in combination. After the reaction, these monomers having been used as solvent will be part of the macromolecular network finally obtained, their integration being wider when dealing with bi-functional monomers. The material obtained after irradiation is now free of products having a low molecular weight and a substantial vapour tension, or capable of contaminating objects with which the polymer is in contact. By way of example, a reactive solvent may be selected from mono and divinyl ethers of mono-, di-, tri-, tetra-ethylene and propylene glycols, N-methylpyrolidone, 2-propenylether of propylene carbonate commercially available for example under the commercial designation PEPC from ISP, New Jersey, United States.

To irradiate the reaction mixture, the irradiation may be selected from ultraviolet radiation, visible radiation, X-rays, γ rays and β radiation. When ultraviolet light is used as actinic radiation, it may be advantageous to add to the photoinitiators of the invention photosensitizers intended to provide an efficient photolysis with wavelengths less energetic than those corresponding to the maximum of absorption of the photoinitiator, such as those produced by industrial devices, (I≈300 nm for mercury vapour lamps in particular). Such additives are known, and by way of non-limiting example, there may be mentioned anthracene, diphenyl-9,10-anthracene, perylene, phenothiazine, tetracene, xanthone, thioxanthone, acetophenone, benzophenone, 1,3,5-triaryl-2-pyrazolines and derivatives thereof, in particular derivatives which are substituted on the aromatic nuclei by alkyl, oxa- or aza-alkyl radicals, enabling inter alia to change the absorption wavelength. Isopropylthioxantone is an example of preferred photosensitizer when an iodonium salt according to the invention is used as photoinitiator.

Among the different types of radiation mentioned, ultraviolet radiation is particularly preferred. On the one hand, it is more convenient to use than the other radiations mentioned. On the other hand, photoinitiators are in general directly sensitive towards UV rays and photosensitizers are more efficient when the difference of energy ($\delta\lambda$) is lower.

The ionic compounds of the invention may also be used in association with free radical initiators produced thermally or by action of actinic radiation. It is also possible to polymerize or cross-link mixtures of monomers or polymers containing functions in which the types of polymerization are different, for example, monomers or prepolymers which polymerize by free radical and monomers or prepolymers which polymerize by cationic polymerization. This possibility is particularly advantageous to produce interpenetrated networks having physical properties which are different from those which would be obtained by a simple mixture of polymers originating from corresponding monomers. Vinyl ethers are not or are very little active by free radical initiation. It is therefore possible, in a reaction mixture containing a photoinitiator according to the invention, a free radical initiator, at least one monomer of the vinyl ether type and at least one monomer comprising non-activated double bonds such as those of the allyl groups, to carry out a separate polymerization of each type of monomer. On the other hand, it is known that monomers which are lacking in electrons, such as esters or amides of furmaric acid, maleic acid, acrylic or methacrylic acid, itaconic acid, acrylonitrile, methacrylonitrile, maleimide and derivatives thereof, form in the presence of vinyl ethers which are enriched in electrons, complexes of transfer of charge giving alternated polymers 1:1 by free radical initiation. An initial excess of vinyl monomers with respect to this stoichiometry enables to preserve polymerizable functions by pure cationic initiation. The start of the activity of a mixture of free radical initiator and cationic initiator according to the invention may be carried simultaneously for the two reactants in the case for example of isolation by actinic radiation of a wavelength for which the photoinitiators of the invention and the selected radical initiators are active, for example at $\lambda$=250 nm. By way of example, the following commercial products: Irgacure 184®, Irgacure 651®, Irgacure 261®, Quantacure DMB®, Quantacure ITX® may be mentioned as initiators.

It may also be advantageous to use the two types of polymerization in a sequential manner, to first form prepolymers which are easy to shape and in which hardening, adhesion, solubility as well as degree of cross-linking may be modified by initiating the activity of the cationic initiator. For example, a mixture of a thermo-dissociable radical initiator and a cationic photoinitiator according to the invention enables to provide sequential polymerizations or cross-linking, first under the action of heat, then under the action of actinic radiation. Similarly, if a free radical initiator and a cationic photoinitiator according to the invention are selected, the first being photosensitive at longer wavelengths than the one initiating the photoinitiator according to the invention, there is obtained a cross-linking in two controllable steps. Free radical initiators may for example be Irgacure® 651 enabling to initiate free radical polymerizations at wavelength of 365 nm.

The invention also has as an object the use of ionic compounds of the invention for chemical amplification reactions of photoresists in the field of microlithography. During such use, a film of a material comprising a polymer and an ionic compound of the invention is subject to irradiation. The irradiation causes the formation of the acid by replacement of the cation M with a proton, which catalyzes the decomposition or transformation of the polymer. After decomposition or transformation of the polymer on the parts of the film which have been irradiated, the monomers formed or the polymer which has been converted are removed and what remains is an image of the unexposed parts. For this particular application, it is advantageous to use a compound of the invention which is in the form of a polymer consisting essentially of styrenyl recurring units carrying an ionic substituent —$C(CN)_2^-$. These compounds enable to obtain after photolysis products which are not volatile, and therefore not odoriferous when dealing with sulfides. Among the polymers which may thus be modified in the presence of a compound of the invention, there may for example be cited polymers containing ester units or tertiaryalkyl arylether units, for example poly (phthaldehydes), polymers of bisphenol A and a diacid, polytertiobutoxycarbonyl oxystyrene, polytertiobutoxy-α-methyl styrene, polyditertiobutylfumarate-co-allyltrimethylsilane and polyacrylates of a tertiary alcohol, in particular tertiobutyl polyacrylate. Other polymers are described in J. V. Crivello et al, Chemistry of Materials 8, 376–381, (1996).

The ionic compounds of the present invention, which have an elevated thermal stability, give numerous advantages with respect to the known salts of the prior art. They have speeds of initiation and propagation which are comparable or higher than those obtained with coordination anions of the type $PF_6^-$, $AsF_6^-$ and especially $SbF_6^-$. In addition, the coefficient of diffusion of the anion —$C(CN)_2^-$ is higher than that of hexafluorometallate anions or tetrafluoroborate anions or phenylborate anions. These properties are explained by the delocalization of the negative charge and the weak repulsion between the partial charges carried by the nitrogen atoms of nitrile groups and removed from one another by 2Å.

In the compounds of the present invention, the pairs of ions have a very high dissociation, which enables the expression of intrinsic catalytic properties of the cation $M^{m+}$, in which the active orbits are easily exposed to substrates of the reaction, especially in different media. Most of the important reactions of organic chemistry may thus be carried out under easy conditions, with excellent yields and the possibility of separating the catalyst from the reaction mixture. The demonstration of asymmetric induction by the use of an ionic compound according to the invention which carries a chiral group is particularly important in view of its generality and its ease of operation. The present invention consequently has as another object the use of compounds of the invention as catalysts in Friedel-Crafts reactions, Diels-Alder reactions, aldolization reactions, additions of Michael, reactions of allylation, reactions of pinacolic coupling, reaction of glycosilation, reaction of openings of the cycle of oxetanes, reactions of metathesis of alkenes, polymerizations of the Ziegler-Natta type, polymerizations of the metathesis type by cycle opening and polymerizations of the metathesis type of acyclic dienes. The preferred ionic compounds of the invention for utilization as catalyst for the above reactions are those in which the cation is selected from lithium, magnesium, copper, zinc, tin, trivalent metals, including rare earths, platinoids, and their organometallic couples, in particular metallocenes.

The compounds of the invention may also be used as solvent to carry out chemical, photochemical, electrochemical, photoelectrochemical reactions. For this particular use, the ionic compounds in which the cation is an imidazolium, triazolium, pyridinium or 4-dimethylamino-pyridinium, are preferred, said cation possibly carrying a substituent on the carbon atoms of the cycle. Among the compounds used in liquid form, those having a melting point lower than 150° C., more particularly lower than 100° C., are particularly preferred.

The inventors have also found that the ionic charge carried by the group $-C(CN)_2^-$ have a stabilizing effect on the electronic conductors of the conjugated polymer type, and that the use of the compound in which the substituent Z comprises a long alkyl chain enables to make these polymers soluble in known organic solvents even in doped state. Grafting of these charges on the polymer itself gives polymers with global cationic charge, which are soluble and present, in addition to their stability, anti-corrosion properties towards metal, such as aluminum and ferrous metals. It is an object of the present invention to provide materials with electronic conduction comprising an ionic compound of the present invention in which the cationic part is a polycation consisting of a doped "p" conjugated polymer. The preferred ionic compounds for this application are those in which the substituent Z or $R_D$ contains an alkyl chain having 6 to 20 carbon atoms.

The coloring materials of cationic type (cyanines) are used more and more frequently as sensitizers of photographic films, for storing optical information (optical disks accessible in writing), for lasers. The tendency of these conjugated molecules to pile over one another when they are in solid phase limits their utilization, because of the variation of the optical properties with respect to the isolated molecule. The use of ionic compounds of the invention for manufacturing cationic coloring materials including counter ions, possibly bound to this same molecule, correspond to functions of the invention enables to reduce phenomenons of aggregation, including in solid polymer matrices and to stabilize these coloring materials. It is another object of the present invention to provide a composition of cationic coloring material, characterized in that it contains an ionic compound according to the invention. The particularly preferred ionic compounds for this application are those in which the negative charge(s) of the anionic group $-C(CN)_2^-$ are either fixed to the molecule of the coloring material, or they constitute the counter-ion of the positive charges of the coloring material.

A few examples of compounds according to the invention are given hereinafter:

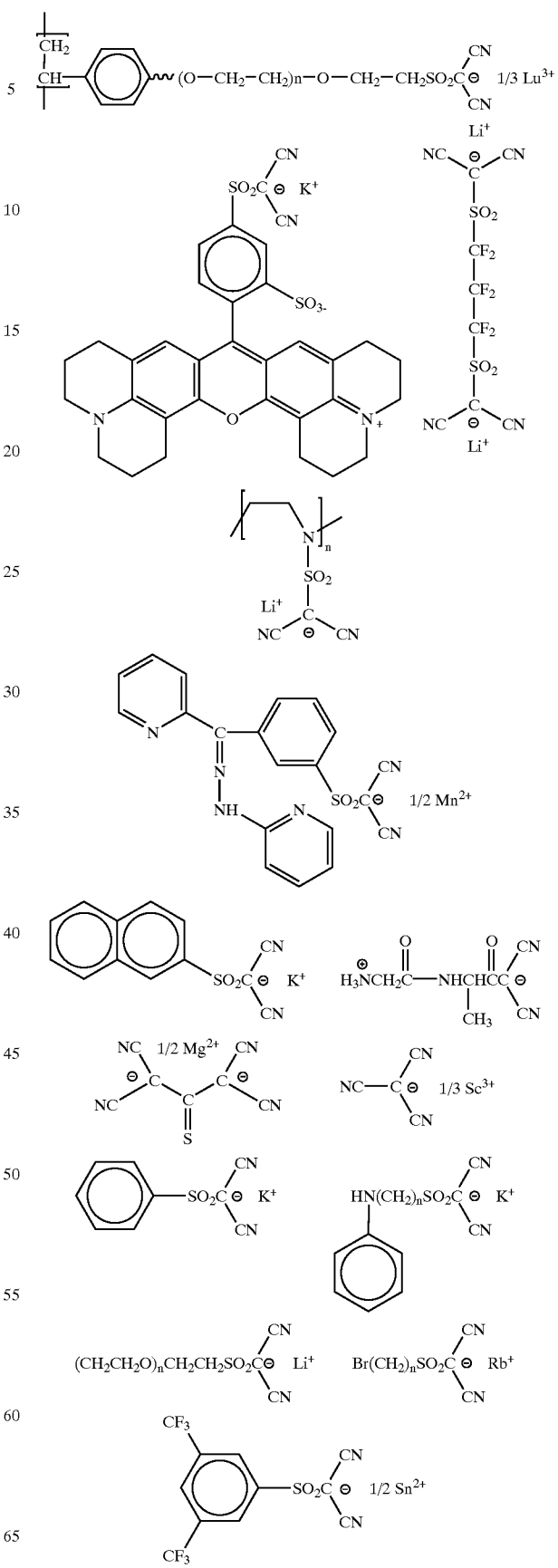

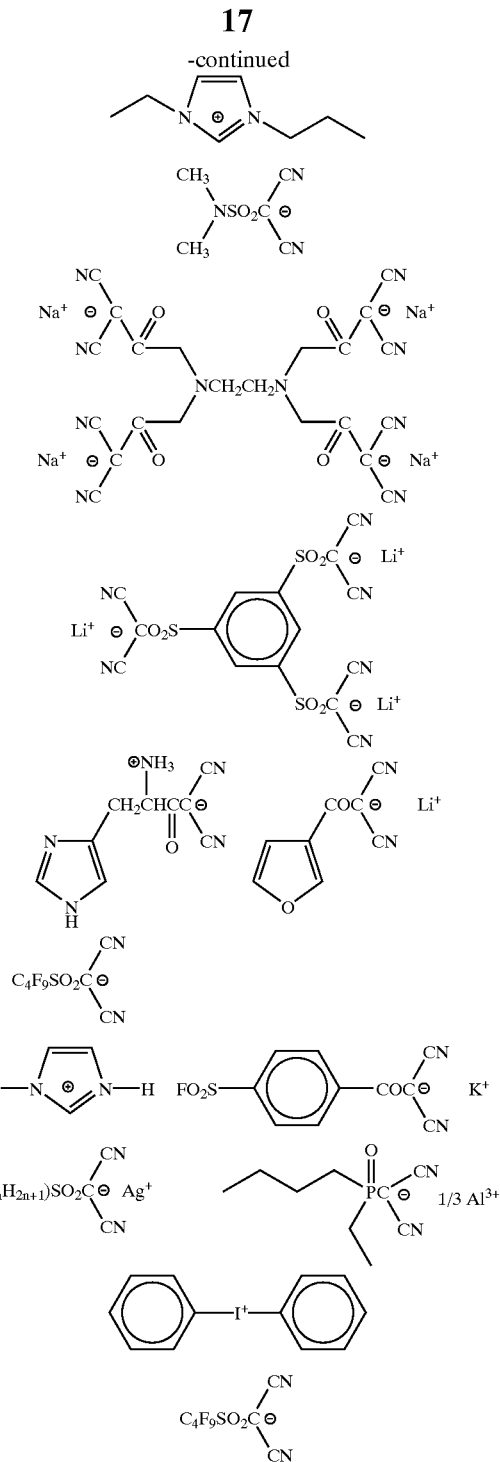

The present invention is explained more in detail with the following examples, which describe the preparation and various utilizations of compounds of the invention. The invention is, however, not limited to these examples.

All the compounds of the invention have been prepared from alkali metal salts of malononitrile. Said salts have been obtained from commercial malononitrile previously purified in a sublimation cell at 40° C. under secondary vacuum, the malononitrile being recovered after 48 hours on the cold finger of the cell, in the form of white crystals which are thereafter kept under argon.

The lithium salt was obtained by dosing an aqueous solution of malononitrile with a titrated solution of lithium hydroxide LiOH, the neutralization point being determined by means of a pH-meter. The aqueous solution was thereafter lyophilized, and the product was dried under secondary vacuum at room temperature during 72 hours. There is obtained a lithium salt which, kept under argon, has a purity determined by a proton and carbon RMN higher than 99%.

By the same process, sodium and potassium salts were obtained by replacing lithium hydroxide respectively with sodium hydroxide and potassium hydroxide.

EXAMPLE 1

3.03 g (10 mmoles) of stearic acid chloride $C_{17}H_{35}COCl$ in 25 ml of tetrahydrofurane (THF) and 5 ml of anhydrous pyridine were added to 1.04 g (10 mmoles) of the potassium salt of malononitrile in 25 ml of tetrahydrofurane. After 24 hours under stirring, the solution was filtered to remove the precipitate of potassium chloride, and was contacted with 500 mg of lithium carbonate $Li_2CO_3$. The mixture was stirred during 24 hours, then the excess of carbonate was removed by centrifugation, and the solvent was evaporated. There is obtained 3.3 g of the lithium salt of malononitrile stearoyl having a purity characterized by a proton and carbon RMN higher than 97%.

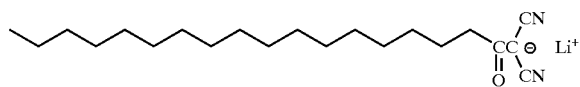

The higher alkyl radical $R_D$ of this salt give it noted tensio-active properties, including in solvents and aprotic solvating polymers.

EXAMPLE 2

To 6.61 g (100 mmoles) of malononitrile in solution in 50 ml of THF at −20° C., there is added in portions 795 mg of lithium hydride LiH. After 2 hours at −20° C., there is added 20.14 g (100 mmoles) of 1-(trifluoromethanesulfonyl) imidazole (commercially available from Fluka). The reaction is continued during 4 hours at −20° C., and 48 hours at room temperature. The solvent was then evaporated and the white solid residue was washed with dichloromethane to remove the imidazole formed during the reaction. There is obtained $LiCF_3SO_2C(CN)_2$.

EXAMPLE 3

Under an atmosphere of argon, there is added 0.66 g (10 mmoles) of malononitrile and 180 mg of lithium anhydride to a solution of 3.02 g (10 mmoles) of nonafluorobutane-sulfonyl in 20 ml of anhydrous THF, kept at 0° C. After 4 hours, the reaction mixture was filtered, evaporated, reclaimed in 10 cm³ of water, and poured into a saturated solution of KCl. The precipitate of $KC_4F_9SO_2C(CN)_2$ was purified by crystallization in water, and in a pentanone/dichloroethane mixture. The yield of analytically pure product is 65%. In a similar manner, there is prepared $KC_6F_{13}SO_2C(CN)_2$ and $KC_{18}F_{17}SO_2C(CN)_2$. The lithium salts were thereafter obtained by ion exchange with LiCl or $LiBF_4$ in THF. These products have noted tensio-active properties, they are soluble in solvating polymers while giving conductive complexes and they provide tensio-static properties.

EXAMPLE 4

324 mg (1 mmole) of 4-dimethylamino)azobenzene-4'-sulfonyl chloride in 5 ml of tetrahydrofurane were added to 104 mg (1 mmole) of the potassium salt of malononitrile in 5 ml of THF and 500 µl of triethylene. After 24 hours under stirring, the precipitate of potassium chloride was removed and, after evaporating the solvent, there is obtained the triethylammonium salt which was suspended in 5 ml of an aqueous solution containing 350 mg of tetrabutylammonium bromide. The mixture was stirred during 24 hours. There is obtained a powder of orange color, which had a purity characterized by proton and carbon RMN higher than 98%, which is soluble in most of the organic solvents, and which corresponds to the following formula:

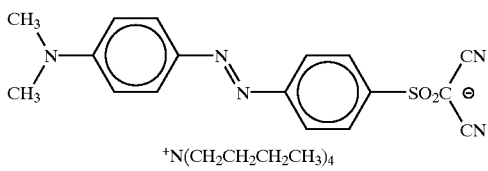

This ionic coloring material is a pH indicator in a non-aqueous medium (yellow-orange—red-violet transition in the pH zone 1–4).

EXAMPLE 5

10.85 g (100 mmoles) of methoxyacetic acid chloride were diluted in 150 ml of acetonitrile and 15 ml of anhydrous pyridine. The mixture was kept under a nitrogen atmosphere and magnetic stirring, and there are added, in portions, 10.41 g (100 mmoles) of the potassium salt of malononitrile. When precipitation of potassium chloride was terminated (about 1 hour), there is added 25 g of anhydrous tripotassium phosphate $K_3PO_4$ and the mixture was stirred during 24 hours. The mixture was thereafter evaporated to dryness. The potassium salt of methoxyacetylmalononitrile obtained was purified by recrystallization in butanone/1,2-dichloroethane mixture.

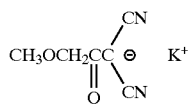

This compound is soluble in most of the usual organic solvents (tetrahydrofurane, acetonitrile, dimethylformamide, ethyl acetate, glymes, . . . ) and in aprotic solvating polymers.

176.2 mg of this compound were dissolved in 5 ml of dry acetonitrile, to which there is added 31.7 mg of anhydrous magnesium chloride. The mixture was stirred during 4 hours and the precipitate of potassium chloride was removed by centrifugation. The floating solution contains the potassium salt of an anionic complex of magnesium $\{Mg[CH_3OCH_2COC(CN)_2]_3\}^-K^+$.

To this floating solution, there is added 800 mg of the random copolymer ethylene oxide (80%)—methyl-glycidyl-ether (20%) of molecular weight $M_w=2.5\times10^5$. By spreading and evaporation of the viscous solution, there is obtained a film of polymer electrolyte containing magnesium in the form of a complex $\{Mg[CH_3OCH_2COC(CN)_2]_3\}^-$.

A primary generator comprising a magnesium anode was made as follows:

| anode | Electrolyte | Cathode |
|---|---|---|
| Mg | polymer electrolyte with anionic vehicular mechanism carrying Mg ions | composite: graphite fluoride-electrolyte-acetylene black |

The electrolyte is the film of polymer electrolyte containing the complex $\{Mg[CH_3OCH_2COC(CN)_2]_3\}^-$ as described above. The positive electrode was obtained in the following manner: a composition was prepared containing 42% v/v of an electrolyte identical to the one described above, 8% v/v of acetylene black and 50% v/v of graphite fluoride $CF_x$ ($x\leq1$); this composition was diluted in acetonitrile, then spread on a sheet of polypropylene 8 µm thick metallized with 200 nm of copper, so as to form a layer about 80 µm thick. The negative electrode was a sheet of magnesium 20 µm thick. The voltage of the battery after assembling by lamination of the elements at 80° C. was 2.5 V and the capacity for a flow of 400 µA/cm² was 7 mAh/cm².

EXAMPLE 6

A sulfonated oligomer of poly (ethylene oxide) PEO was prepared in the following manner: 10 g of PEO of molecular weight 600 were dried by azeotropic distillation with benzene and lyophilization. After adding 50 ml of THF, the terminal groups OH were metallized with potassium-naphthalene. The stoichiometry was determined by colorimetry, the end of the reaction being indicated by a persistence of an intense green color of the anion radical of naphthalene. 4.10 g of propanesultone were then added. After evaporation of the solvent, the α,ω)-disulfonated polymer was obtained in the form of powder, and the residual naphthalene was removed by washing with hexane.

5 g of the α,ω-disulfonated polymer thus formed, in suspension in 15 ml of acetonitrile, were treated with 1.8 g of (chloromethylene)dimethylammonium chloride $[(CH_3)_2N=CHCl]^+,Cl^-$. A precipitate of potassium chloride was formed after about 1 hour. To this suspension 1.26 g of the potassium salt of malononitrile and 3 ml of anhydrous pyridine were added. After filtering, the reaction mixture was stirred in the presence of 2 g of lithium phosphate $Li_3PO_4$. A new filtering has enabled to separate a colorless solution which, by concentration, has given a viscous fluid.

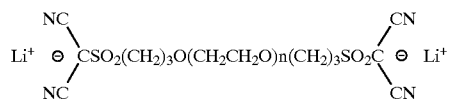

This material enables to plasticize a large number of polymers containing polar units (ether, amide, nitrile, ester.), while giving them a high ionic conductivity.

EXAMPLE 7

A non-ionic tensio-active material, polyoxyethylene-23 lauryl ether $C_{12}H_{25}(OCH_2CH_2)_{23}OH$ (Brij® 35), was sulfonated by a procedure similar to the one of Example 4. 12 g of Brij® 35 were dried by azeotropic distillation with benzene and lyophilization. After adding 50 ml of THF, the OH terminal groups were metallized with sodium hydride in the presence of 5 mg of triphenylmethane. The stoichiometry was determined by colorimetry, the end of the reaction being indicated by a persistence of an intense red color of the anion φ₃C⁻. 1.4 g of 1,4-butanesultone were then added. After evaporation of the solvent, the sulfonated oligomer was obtained in the form of powder.

5 g of the sulfonated oligomer thus formed in suspension in 15 ml of acetonitrile were treated with 1 ml of thionyl chloride and 10 μl of dimethylformamide. A precipitate of sodium chloride was formed in 20 min. After filtering, the solvent and the excess of SOCl₂ were evaporated under reduced pressure. The residue was dissolved in 30 ml of pyridine, then 350 mg of the sodium salt of malononitrile were added. After filtering, the reaction mixture was stirred in the presence of 1 g of lithium phosphate Li₃PO₄. A new filtration has enabled to separate a colorless solution which, by concentration, has given a wax.

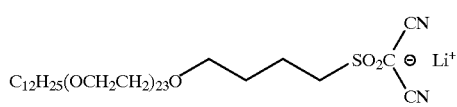

This material has tensio-active and plasticizing properties.

EXAMPLE 8

380 mg (1 mmole) of ethylenebis(oxyethylene-nitrilo) tetraacetic acid in 10 ml of pyridine were treated with 912 mg of hydroxysuccinimidyl carbonate during 24 hours. 416 mg (4 mmoles) of the potassium salt of malononitrile were added into 15 ml of an equal volume mixture of pyridine and acetonitrile. After 24 hours, the precipitate was separated by filtration and washed with 2 portions of 30 ml of THF. There are obtained crystals of:

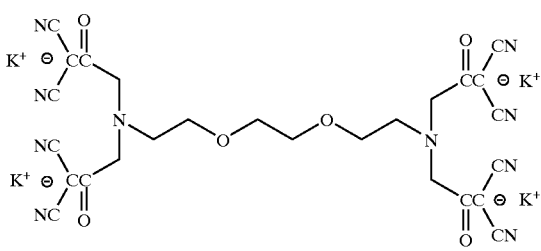

This compound is a ligand (L) of dilvalent ($A^{II}$) and trivalent ($A^{III}$) metals, in particular rare earths. The corresponding complexes $[A^{III}L]^{2-}M^{+}$ and $[A^{III}L]^{-}M^{+}$ are salts which are soluble in polar aprotic media and in polar polymers, in particular polyethers. These complexes in which the central metal A is protected from outside electrostatic influences are interesting for constituting lasers. They also permit redox reactions by changing the degree of oxidation of the metal A.

EXAMPLE 9

A solution of 548 mg (2 mmoles) of 1,1'-ferrocenedicarboxylic acid and 824 mg (4 mmoles) of dicyclohexylcarbodiimide in 5 ml of an equal volume mixture of anhydrous pyridine and methanol was prepared. The mixture was kept under magnetic stirring at room temperature during 75 hours. Then, there is added 288 mg (4 mmoles) of the lithium salt of malononitrile. The mixture was kept under stirring at room temperature during 24 hours. The precipitate of dicyclohexylurea was removed by centrifugation and the solution was evaporated. There is obtained a product 1,1'-ferrocene-diacetylmalononitrile in the form of an hydroscopic dark brown solid, having a purity characterized by a proton and carbon RMN higher than 98%. It is soluble in most of the usual organic solvents (tetrahydrofurane, acetonitrile, dimethylformamide, ethyl acetate, glymes, . . . ) and in aprotic solvating polymers.

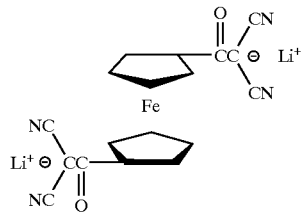

This salt has a reversible redox couple. In polyethylene oxide, it is possible to determine, on an electrode of platinum of a diameter of 125 μm, a reversible potential ≈3.8 V with respect to a lithium electrode.

By dissolution in a liquid, gel or polymer electrolyte, it enables to provide a protection in surcharge in lithium batteries, thus acting as a redox shuttle. It also permits to provide electrical systems with coloring materials.

EXAMPLE 10

501 mg (2 mmoles) of 6-hydroxy-2,5,7,8-tetramethylchroman-2-carboxylic acid (Trolox):

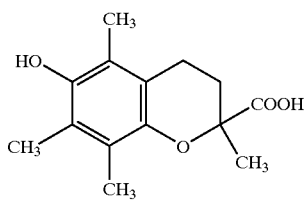

were suspended in 10 ml of an equal volume mixture of an anhydrous pyridine and methanol with 313 μl (2 mmoles) of 1,3 diisopropylcarbodiimide. After 24 hours, the precipitate of diisopropylurea was filtered and 208 mg (2 mmoles) of the potassium salt of malononitrile were added. The mixture was kept under stirring in a neutral atmosphere (nitrogen) during 24 hours. The volume of the solution was reduced to 2 ml by means of a rotary evaporator. 20 ml of dioxane were added and the mixture was cooled at −10° C. A white precipitate was collected by filtering. The analysis corresponds to $C_{17}H_{17}N_2O_3K$.

This product has anti-oxidizing properties, in particular for polymers. The same is true with respect to derivatives of other cations, including organic cations such as tetraalkylammonium cations.

EXAMPLE 11

2.8 g (10 mmoles) of 4,4'-azobis(4-cyanaovaleric) acid, 3.24 g (20 mmoles) of carbonyldiimidazole and 100 mg of dimethylamino pyridine were suspended in 20 ml ether and kept at 0° C. After $CO_2$ has ceased to escape (5 hours), there is added 1.44 g (20 mmoles) of the lithium salt of malononitrile. The mixture was kept under mechanical stirring at 0° C. during 1 hour. By centrifugation, the following crystalline precipitate was isolated:

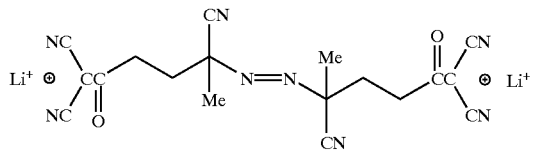

This salt is soluble in particular in acetone, acetonitrile, ethyl acetate, tetrahydrofurane. It may be used as a free radical initiator to initiate polymerization or cross-linking reactions already at 60° C.

EXAMPLE 12

479 mg (1 mmole) of Rhodamine B were suspended in 10 ml of pyridine and 104 mg (1 mmole) of the potassium salt of malononitrile, and 206 mg (1 mmole) of dicyclohexyl-carbodiimide were added. After 48 hours under stirring, the mixture was filtered to remove dicyclohexylurea and was subjected to evaporation. The compound obtained is a zwitterion which has intense coloring properties. It is soluble in polar polymers and enables to provide lasers with coloring materials. The acetylmalononitrile group also enables it to be adsorbed on oxides, in particular nano-particulate titanium dioxide, it then acts as a sensitizer towards visible radiation, in particular in applications to photovoltaic cells.

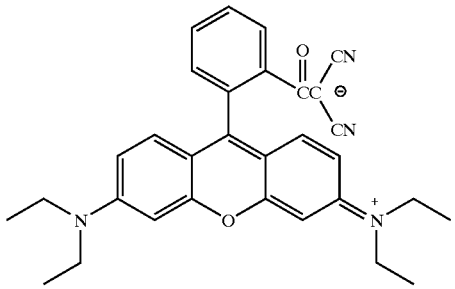

EXAMPLE 13

Pyrryl-3 acetic acid (M=122) was prepared according to the method of D. Delabouglise (Theses Universite de Paris-Nord, February 1991, "Molecular Control of Properties of Polymers"). 488 mg of this compound were dissolved in a mixture of 5 ml of acetonitrile and 1 ml of pyridine, to which there it added 648 mg (40 mmoles) of carbonyldiimidazole. After 24 hours and at the end of $CO_2$ escape, there is added 417 mg (40 mmoles) of the potassium salt of malononitrile. The mixture was stirred during 48 hours at room temperature. The solvent was evaporated and the potassium salt was purified by recrystallization in the mixture butanone-1,2 dichloroethane.

There is prepared 10 ml of a solution $5.10^{-2}$ M in acetonitrile, of the salt obtained and an electropolymerization was carried out in the anode compartment of an electrochemical cell on a platinum electrode. There is obtained a flexible conductive film in which the doping (oxidation) is ensured by exchange of cations and electrons with the outside. The conductivity of this material is of the order of $10$ $S.cm^{-1}$ and it is stable in ambient atmosphere. The electropolymerization carried out in the presence of non-substituted pyrol or having oxyethylene chains in N or 3 position gives copolymers which are also stable in which the change of color may be used for providing an electrochrome system:

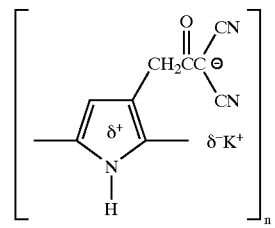

EXAMPLE 14

By operating in a glove box under argon, to 24.15 g (100 mmoles) of di-2-ethylhexylamine in 100 ml of THF at −20° C., there is added in portions 32 ml of butyllithium 2 M in cyclohexane (100 mmoles). After 1 hour, there is added 11.85 g (100 mmoles) of chlorosulfonyl fluoride $FSO_2Cl$. The reaction was continued for 4 hours at −20° C., and during 24 hours at room temperature. The temperature was then brought to 0° C. and there is added 10.42 g (100 mmoles) of the potassium salt of malononitrile $KHC(CN)_2$ and 11.22 g (100 mmoles) of DABCO. After 24 hours at 0° C., the reaction mixture was filtered to remove the precipitate of potassium chloride and the hydrochloride of DABCO. After evaporation of the solvent and drying, the lithium salt of di-2-ethylhexylaminosulfonylmalononitrile was recovered, with a purity characterized by a proton and carbon RMN higher than 98%.

According to the same process, the lithium salt of dibutylaminosulfonylmalononitrile was obtained from dibutylamine.

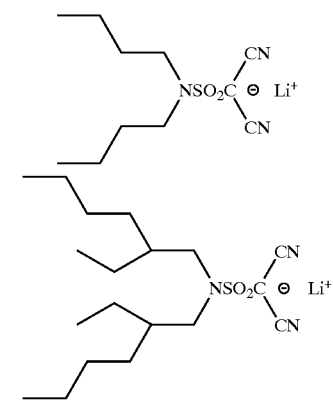

Potassium salts were obtained by treating the lithium salts in the minimum amount of water with potassium fluoride KF. After filtration, evaporation and drying, quantitative amounts of potassium salts were recovered.

These salts are soluble in most of the usual organic solvents (tetrahydrofurane, acetonitrile, dimethylformamide, ethyl acetate, glymes, . . . ) and in aprotic solvating polymers.

EXAMPLE 15

5.44 g (10 mmoles) of 3,3'-diethyl-thiatricarbocyanine (commercially available from Aldrich, Milwaukee, USA) and 4.08 g (10 mmoles) of the potassium salt of di-2-ethylhexylaminosulfonylmalononitrile prepared according to Example 14 were stirred together during 24 hours in water. By extraction of the aqueous phase with dichloromethane, 3,3'-diethylthiatricarbocyanine of di-2-ethylhexylaminosulfonylmalononitrile was recovered, with a purity characterized by a proton RMN higher than 99%.

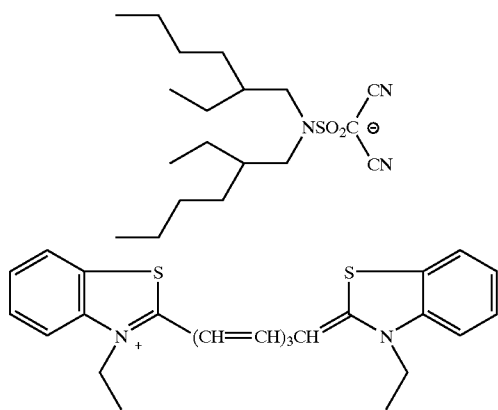

This salt is highly soluble in low polar solvents such as dichlorolmethane or methylene chloride as well as in low polar matrices such as methylpolymethacrylate.

When it is used as a coloring material, a very distinct decrease of the aggregation of molecules of coloring material is noted, due to the "plasticizing" character of different dialkylamino groups, which constitutes an advantage. As a matter of fact, the phenomenon of aggregation is prejudicial to the good operation of systems utilizing coloring materials, in particular in optical disks for storing information, since it causes a widening of the optical absorption bands.

EXAMPLE 16

3.17 g (10 mmoles) of diphenyliodonium chloride $(C_6H_5)_2ICl$ and 4.08 g (10 mmoles) of the potassium salt of di-2-ethylhexylaminosulfonylmalononitrile prepared according to Example 14 were stirred together during 24 hours in water. By extraction of the aqueous phase with dichloromethane, di-2-ethylhexyl-aminosulfonylmalononitrile diphenyliodonium was recovered, with a purity characterized by a proton RMN higher than 99%.

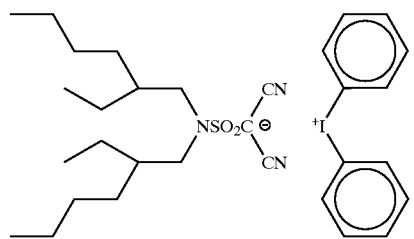

This salt enables to initiate, under the effect of an actinic radiation (light, y rays, electron beams), the reaction of cationic cross-linking of monomers rich in electrons (vinyl ethers, propylvinyl ethers, . . . )

It is soluble in most of the usual organic solvents (tetrahydrofurane, acetonitrile, dimethylformamide, ethyl acetate, glymes, . . . ) and in aprotic solvating polymers such as polyethylene oxide. It is also soluble to the extent of 5% by weight in reactive solvents such as triethyleneglycol divinyl ether, contrary for example to the bis (trifluoromethanesulfonyl)imide diphenyliodonium salt.

The photoinitiating properties of this salt were tested by irradiating with a UV radiation at 254 nm, a power of 1,900 mW/cm$^2$, a non-woven felt of polyethylene soaked with triethyleneglycol divinyl ether (79% by weight) containing di-2-ethylhexylaminosulfonylmalononitrile diphenyliodonium (1% by weight) of the present example and 7,8-octene-3,6-oxa-1-sulfonylmalononitrile is (20% by weight), obtained in Example 21. After a period of a few seconds under irradiation, followed by a period of 10 min enabling the propagation of species produced in the medium (postcure), there is obtained a polyelectrolyte supported by the felt. This type of composite is very interesting for the development of lithium batteries with polymer or gel electrolyte.

EXAMPLE 17

5.91 g (20 mmoles) of the potassium salt of dibutylaminosulfonylmalononitrile, prepared according to Example 14, were placed in solution in 10 ml of water. Under stirring, 2.71 g (10 mmoles) of 2,2'-azobis(2-methylpropionamidine) hydrochloride [=NC(CH$_3$)$_2$C (=NH)NH$_2$]$_2$.2HCl] (commercially available from Aldrich) in solution in 10 ml of water were added. There is immediately formed a precipitate which is collected by filtration. After drying under vacuum at room temperature, 2,2'-azobis (2-methylpropionamidine) dibutylaminosulfonylmalononitrile was recovered.

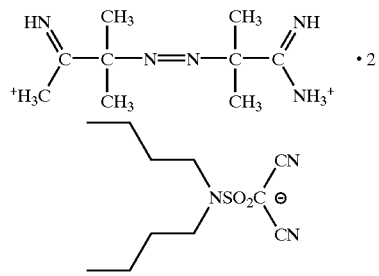

This salt is a free radical polymerization initiator which is soluble in most of the usual organic solvents (tetrahydrofurane, acetonitrile, dimethylformamide, ethyl acetate, glymes, . . . ) and in aprotic solvating monomers and polymers, contrary to 2,2'-azobis(2-methylpropionamidine) hydrochloride.

There is prepared a solution in acetonitrile of 1 part of the initiator and 100 parts of a polymer containing ethylenic unsaturations, obtained by polycondensation of polyethylene glycol of molecular weight 1,000 with 3-chloro-2-chloromethyl-1-propene according to the procedure described by Alloin, et al (*Solid States Ionics*, (1993), 60, 3). The viscous solution obtained was poured onto a polypropylene (PP) film. After evaporating the solvent, the polymer film of a thickness of 110 µm on PP was stored for one week in a glove box under argon to dry the same. Cross-linking was then. initiated by bringing the temperature of the film to 60° C. After one night, there is obtained a film having good mechanical properties and a small amount of extractable materials (lower than 1%). The solubility of the initiator used in the polymer matrix therefore enables to obtain an efficient and homogeneous cross-linking. Moreover, this initiator, contrary for example to 2,2'-azobisisobutyronitrile, is not volatile and the quantity added may at best be optimized for each type of polymerization.

EXAMPLE 18

To 4.8 g (10 mmoles) of the potassium salt of di-2-ethylhexylaminosulfonylmalononitrile, obtained in Example 14, in solution in 10 ml of anhydrous nitromethane, there is added in a glove box 1.17 g (10 mmoles) of nitrosonium tetra-fluoroborate $NOBF_4$ (commercially available from Aldrich). After one hour, the reaction mixture was filtered to remove the insoluble potassium tetrafluoroborate, and there is obtained a 1 M solution of the nitrosonium salt of di-2-ethylhexylaminosulfonylmalononitrile in nitromethane.

By a similar process, there is prepared a 1 M solution in nitromethane of the nitrosonium salt of dibutylaminosulfonylmalononitrile, from the potassium salt of dibutylaminosulfonylmalononitrile. These salts are particularly interesting for doping conjugated polymers (polythiophene, polypyrrole, polyaniline, . . . ) to which they give an appreciable electronic conductivity.

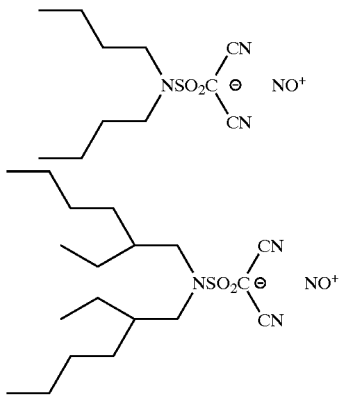

There are provided two deposits of poly (3-hexylthiophene) (commercially available from Aldrich, Milwaukee, USA) on glass plates from a chloroform solution. After drying, these deposits were respectively doped with the above salts in solution in nitromethane. After doping, each of the films of poly (3-hexylthiophene) thus obtained had an electronic conductivity higher than 1 $S.cm^{-1}$ and a good stability in humid medium. These deposits were interesting for providing masks in the semi-conductor industry.

EXAMPLE 19

In 100 ml of anhydrous tetrahydrofurane under argon at 0° C., 20.27 g (100 mmoles) of 4-styrenesulfonyl chloride $CH_2$=$CHC_6H_4SO_2Cl$ (commercially available from Monomer-Polymer & Dajac Laboratories), 10.42 g (100 mmoles) of malononitrile and 22.44 g (200 mmoles) of DABCO were reacted. After 2 hours at 0° C. and 48 hours at room temperature, the solution was filtered to remove the DABCO hydrochloride formed, and it was treated with 4.24 g of anhydrous lithium chloride (100 mmoles), stored and weighed in a glove box. There is immediately formed a precipitate of DABCO hydrochloride and the reaction mixture was then again filtered after stirring for 6 hours. After evaporation and drying under vacuum during 24 hours at room temperature, 31.16 g of the lithium salt of 4-styrenesulfonylmalononitrile were recovered, with a purity characterized by a proton and carbon RMN higher than 97%.

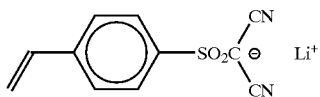

This salt may be homo- or copolymerized by means of a polymerization initiated by anionic, cationic or free radical means. It may also be grafted by irradiation on a polymer matrix such as vinylidene polyfluoride. The homopolymer, obtained by free radical polymerization in deaerated water initiated by cyanovaleric acid at 60° C., is soluble in the usual organic solvents and in aprotic solvating polymers. In polyethylene oxide at a concentration O/Li of 16/1, this salt has a conductivity ≈5.2×$10^{-4}$ $S.cm^{-1}$ at 100° C.

Moreover, in a concentrated solution in acetone (≈1 M of lithium cation), this homopolymer of the lithium salt of 4-styrenesulfonylmalononitrile may be used as a catalyst for Diels-Alder reactions.

EXAMPLE 20

According to a process similar to the one described in Example 19, the lithium salt of vinylsulfonylmalononitrile was obtained from 11.01 g (100 mmoles) of ethylenesulfonyl fluoride (commercially available from Fluka, Buchs, Switzerland), with a purity characterized by a proton and carbon RMN higher than 98%.

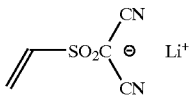

This salt may be homo- or copolymerized by means of a free radical initiated polymerization.

Thus, 6.6 g of a copolymer of ethylene oxide containing allyl double bonds and having a molecular weight $M_w$=2.5×$10^5$ were placed in solution in acetonitrile. 1.52 g of the lithium salt of vinylsulfonylmalononitrile and 50 mg of the free radical initiator prepared according to Example 17 were added. The solution was evaporated in a cupel of PTFE with flat bottom, and the container was placed in an oven under a primary vacuum at 80° C. during 12 hours. A cross-linked elastomer was obtained on which —$SO_2C(CN)_2Li$ groups are fixed. This material, which constitutes an electrolyte with fixed anions, has a conduction by the lithium ions of 6.7×$10^{-4}$ $S.cm^{-1}$ at 60° C., and a cationic transport number of 0.92.

EXAMPLE 21

To 2.2 g (25 mmoles) of ethyleneglycol vinyl ether $CH_2$=$CHO(CH_2)_2OH$ in 60 ml of anhydrous dimethylformamide, there are added 4.05 g of the lithium salt of vinylsulfonylmalononitrile, obtained in Example 20, 5.87 g (42.5 mmoles) of anhydrous potassium carbonate $K_2CO_3$ and 330 mg (1.25 mmole) of 18-Crown-6 (acting as complexing agent of the cation $K^+$). The reaction mixture was then stirred under argon at 80° C. After 48 hours, the reaction mixture was filtered on a fritted glass of porosity N° 3, and the solvent was removed by evaporation under reduced pressure. After drying, the residual compound was recrystallized in 10 ml of water containing 1.86 g (25 mmoles) of anhydrous potassium KCl. After filtration and drying, the potassium salt of 7,8-octene-3,6-oxa-1-sulfonylmalononitrile was recovered, with a purity characterized by a proton and carbon RMN higher than 98%.

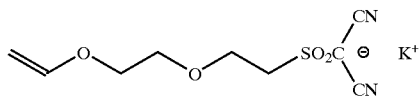

The lithium salt was obtained in quantitative yield by treating the potassium salt in anhydrous tetrahydrofurane with a stoichiometric quantity of anhydrous lithium chloride, filtering of the reaction mixture, evaporation of the solvent and drying under vacuum.

This salt may be homo- or copolymerized through a cation initiated polymerization, by polymerization alternated with an unsaturated monomer initiated by a free radical.

The homopolymer prepared by polymerization in anhydrous acetonitrile initiated by cationic means with bis(trifluoromethanesulfonyl)imide has a conductivity at a concentration of 0.8 M in a mixture of dimethylcarbonate and ethylene carbonate (2:1) of $6 \times 10^{-3}$ S.cm$^{-1}$ at 30° C. Moreover, this homopolymer is soluble in most of the usual organic solvents (tetrahydrofurane, acetonitrile, dimethylformamide, ethyl acetate, glymes, . . . ) and in aprotic solvating polymers such as polyethylene oxide. This homopolymer consequently constitutes a good ionically conductive material.

EXAMPLE 22

To a solution in 10 ml of anhydrous tetrahydrofurane at 0° C. of 4.49 g (40 mmoles) of DABCO and 1.32 g (20 mmoles) of malononitrile, there is added 6.05 g (20 mmoles) of 4-iodobenzenesulfonyl chloride IC$_6$H$_4$SO$_2$Cl (commercially available from Aldrich) diluted in 5 ml of anhydrous tetrahydrofurane. After 2 hours at 0° C., the reaction was continued during 24 hours at room temperature. The DABCO hydrochloride formed during the reaction was removed by filtering on a fritted glass of porosity N° 4. After evaporation of acetonitrile from the filtered solution, the product was reclaimed in 15 ml of cold water and there is slowly added 1.49 g (20 mmoles) of anhydrous potassium chloride in solution in 5 ml of water. A precipitate has appeared which was collected by filtration on a fritted glass of porosity N° 4. After drying, the potassium salt of 4-iodobenzenesulfonylmalononitrile was recovered.

This compound was oxidized into iodosoacetate K[(NC)$_2$CSO$_2$C$_6$H$_4$I(O$_2$CCH$_3$)$_2$] with a mixture of acetic acid, acetic anhydride and hydrogen peroxide according to the method of Yamada & al (*Die Makromolecular Chemie*, (1972), 152, 153–162). 4.88 g (10 mmoles) of said iodosoacetate were suspended in a mixture of 15 ml of methanesulfonic acid and 4.51 g (30 mmoles) of butoxybenzene kept at 0° C. during 4 hours. The reaction product was poured into 300 ml of ether and the precipitate was separated by filtration, washed with ether and dried. There is thus obtained 3.9 g of zwitterion (4-butoxybenzene)-(4-phenylsulfonylmalononitrile) iodonium (75% yield), with a purity characterized by a proton and carbon RMN higher than 97%.

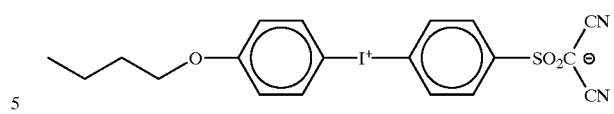

This zwitterion enables to initiate under the effect of actinic radiation (light, g rays, electron beams) a cationic cross-linking reaction of electron enriched monomers (vinyl ethers, vinylpropenyl ethers, . . . ).

It has a good solubility in most of the usual organic solvents (tetrahydrofurane, acetonitrile, dimethylfornamide, ethyl acetate, glymes, . . . ) and in aprotic solvating monomers and polymers such as polyethylene oxide. It is also soluble at more than 5% by weight in reactive solvents such as triethyleneglycol divinyl ether.

The photoinitiating properties of this salt were tested by irradiating with U.V. radiation at 254 nm, a power of 1,900 mW/cm$^2$, a solution of triethyleneglycol divinyl ether containing up to 1% by weight of said iodonium salt. After a few seconds under irradiation, the reactive solvent has solidified, and the reaction was very exothermic.

EXAMPLE 23

A solution of 2.22 g (5 mmoles) of tetrakis(acetonitrile) palladium(II) tetrafluoroborate (CH$_3$CN)$_4$Pd(BF$_4$)$_2$ (commercially available from Aldrich), in 30 ml of tetrahydrofurane, was treated with 4.08 g (10 mmoles) of potassium di-2-ethylhexyl-aminosulfonylmalononitrile. After 24 hours under stirring, the reaction mixture was filtered to remove the precipitate of potassium tetrafluoroborate KBF$_4$ and the solvent was evaporated. There was obtained a quantitative yield of di-2-ethylhexylaminosulfonylmalononitrile of tetrakis (acetonitrile)-palladium(II).

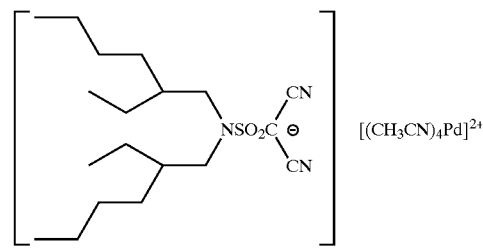

This salt is useful as a catalyst for the vinyl polymerization of norbornene. Thus, norbornene was polymerized at room temperature in nitromethane in the presence of 300 ppm of this salt. After 2 hours, the reaction mixture was reprecipitated in methanol. There is obtained a polynorbornene having an average molecular weight number of 420,000, with a yield of 82%.

EXAMPLE 24

By operating in a glove box under argon, 1.8 g of phenzaine (10 mmoles) and 139 mg of metallic lithium were introduced in a 30 ml polypropylene (Nalgene®) flask. Then 20 ml of anhydrous tetrahydrofurane and small balls of agate were added. The closed flask was then rotated upon itself, outside the glove box, on the shaft of a motor. Tetrahydrofurane rapidly turned into a dark mauve color which characterizes mono-lithium phenazine. After 24 hours, a suspension of an orange precipitate of 9,10-di-Li-dihydrophenazine was obtained. To 8.61 g (20 mmoles) of this compound, 4.89 g (40 mmoles) of 1,3-propane sultone was then added. After 8 hours of crushing at room temperature, the reaction mixture was filtered to remove the small balls of agate and under argon two drops of dimethylformamide were added to the filtered solution, and slowly 5.08 g (40 mmoles) of oxalyl chloride ClCOCOCl in solution in 15 ml of anhydrous dichloromethane. After 4 hours at room temperature, 4.65 g (40 mmoles) of potassium malononitrile were added. The reaction was continued during 24 hours, and the reaction mixture was filtered to remove the precipitate of potassium chloride. After evaporation of the solvent, the di-lithium salt of 9-10-(propylsulfonylmalononitrile) phenazine was recovered, with a purity characterized by a proton and carbon RMN higher than 98%.

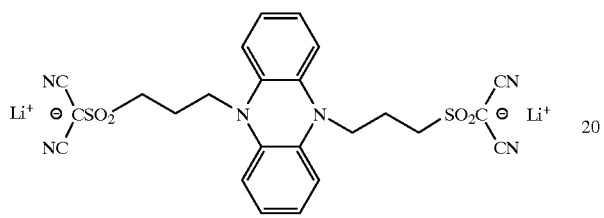

This compound is soluble in most of the usual organic solvents (tetrahydrofurane, acetonitrile, dimethylformamide, ethyl acetate, glymes, . . . ) and in polar polymers.

This compound has two reversible redox couples. In polyethylene oxide, it was possible to show, on a platinum electrode of 125 μm diameter, a first redox couple at a potential ≈3.2 V and a second redox couple at a potential ≈3.8 V, these potentials being measured towards a lithium electrode.

When it is dissolved in a liquid, gel or polymer electrolyte, this compound provides a protection in surcharge in lithium batteries, thus acting as a redox shuttle.

This compound also enables to provide electrochrome systems with coloring materials. In this manner, an electrochrome glazing was produced by depositing on a glass plate, covered with a conductive layer of ITO (indium and tin oxide), an acetone solution of this compound and of poly (benzodiimide-co-ethylene oxide) of a molecular weight ≈1,100 g/mole, obtained by a process similar to the one described in French Patent Application FR 93/01117. After evaporating the solvent and drying, on a previously deposited polymer, in a glove box, a second glass electrode covered with a conductive layer of ITO was assembled. After having sealed this product to make it impervious, a potential of 1,250 mV was applied on the exterior by means of a potentiostat. The system then became colored with an intense blue. By applying a potential of −500 mV, it was possible to note a is relatively fast discoloration of the system (lower than 60 s). Such an electrochrome system is easy to prepare, even for large size systems (larger than m$^2$) which utilize glass as well as a polymer suitably treated as a conductive transparent electrode. Moreover, the energy required to maintain the coloration is relatively weak, lower than 1 W/m$^2$.

EXAMPLE 25

In a Parr chemical reactor, 5.21 g (50 mmoles) of potassium malononitrile and 264 mg of a crown-ether, 18-Crown-6 were placed in solution in 60 ml of anhydrous acetonitrile. After closing the reactor, flushing with argon was carried out during 15 min before isolating the reactor.

Then, there are introduced 6.41 g (50 mmoles) of sulfur dioxide SO$_2$ (commercially available from Fluka) and, after 10 min, 9.52 g (50 mmoles) of vinyltriethoxysilane (commercially available from Fluka) in solution in 20 ml of anhydrous acetonitrile. After 6 hours at room temperature, the temperature of the reactor was brought to 40° C. and the reactor was kept at that temperature during 48 hours, and the solvent was evaporated. After drying under vacuum, the product was stored under argon. the potassium salt of 2-(triethoxysilyl)ethylsulfonylmalononitrile [(C$_2$H$_5$O)$_3$Si (CH$_2$)$_2$SO$_2$C(CN)$_2$)]K was recovered in quantitative yield, with a purity characterized by a proton and carbon RMN higher than 99%.

The lithium salt was obtained by ionic exchange with lithium chloride in tetrahydrofurane.

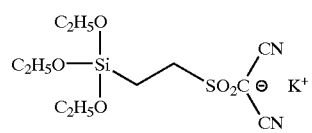

These salts enable to produce organosilicon networks by a mechanism of hydrolysis-polycondensation. They also permit to treat materials based on glass (fibre, glazing, . . . ) in order to modify the state of their surface and in particular to give them antistatic properties.

In addition, homopolymers or copolymers may be obtained with various alkoxysilanes in a protic medium, possibly in the presence of a catalyst, (acid, base, fluoride, . . . ). A copolymer was prepared by polycondensing the potassium salt of 2-(triethoxysilyl) ethylsulfonylmalononitrile with O-[2-(trimethoxysilyl) ethyl]-O'-methylpolyethylene glycol of molecular weight 5,000 (commercially available from Shearwaters Polymers) (5:1) in a water/methanol mixture, by utilizing as catalyst a trace of a perchloric acid. After a few hours, the solution was concentrated. A felt of activated carbon, previously degassed, with a specific surface of 1, 500 m$^2$/g (commercially available from Actitex), was then impregnated with the viscous liquid obtained. After drying, the operation was repeated to improve the impregnation. After one week in a drying oven at 50° C., 2 pastils with a diameter of 2 cm were stamped out. A sheet of cigarette paper (commercially available from Bollore Technologies) was then impregnated with a viscous liquid which is identical to the one used to impregnate the carbon felt mentioned above. This sheet was placed between the two carbon electrodes previously stamped out. After one week in a drying oven at 50° C. and two days under vacuum at 60° C., there is obtained a "all-solid" electrochemical supercapacitance. This supercapacitance has the following characteristics at 40° C.: a density of energy of 15 Wh/l (or a capacity of 96 F/g of carbon for an electrode), a maximum power of 700 W/kg and good results in cycling (more than 10,000 cycles of charge/discharge between 0 and 2V). This type of supercapacitance is particularly interesting for the field of electronics because of the absence of volatile liquids.

EXAMPLE 26

By a process similar to the one described in Example 25, the lithium salt of bis[3-(trimethoxysilyl)propyl] aminosulfonylmalononitrile was synthesized from 12.54 g (40 mmoles) of bis[3-(trimethoxysilyl)propyl]amine [(CH$_3$O)$_3$Si(CH$_2$)$_3$]$_2$NH), (commercially available from Fluka). The compound obtained had a purity characterized by a proton and carbon RMN higher than 98%.

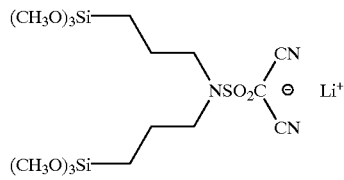

This compound has analogous properties to those of the compounds of Example 25 and may be used for the same applications.

A polycondensation of this compound was carried out in a water/methanol mixture, by utilizing a drop of concentrated hydrochloric acid as catalyst. After a few hours, the solvents were evaporated and the viscous liquid obtained was poured onto a Teflon® plate. After one week in a drying oven at 50° C., the material obtained was dried under vacuum at 100° C. during 48 hours, and was crushed under argon until the particle size was of the order of 1 micron. A to composite electrolyte was then prepared by mixing this powder with polyethylene oxide of molecular weight 300, 000 in acetonitrile. After pouring this dispersion in a glass ring and evaporating acetonitrile, there is obtained a film of composite electrolyte of good mechanical quality, with a thickness of 220 μm. This electrolyte has an ionic conductivity higher than $10^{-5}$ S.cm$^{-1}$ at 60° C. and a cationic transport number of 0.92.

EXAMPLE 27

A solution of 10.81 g (40 mmoles) of the lithium salt of 4-styrenesulfonylmalononitrile prepared as in Example 19, 3.18 g of acrylonitrile (40 mmoles) and 100 mg of 1,1'-azobis(cyclohexanecarbonitrile) in 100 ml of anhydrous tetrahydrofurane was degassed by flushing with dry argon. Under argon, copolymerization of acrylonitrile with the styrene derivatives was carried out by heating the reaction mixture at 60° C. during 48 hours. After cooling, the solution was concentrated, and the polymer was recovered by reprecipitation in ether. After filtration and drying, the lithium salt of poly-(acrylonitrile-co-4-styrenesulfonylmalononitrile) (PANSSM) was obtained.

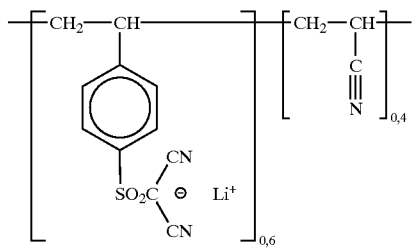

This polymer enables to prepare gelled polymer electrolytes with fixed anions. It constitutes the matrix enabling to obtain the gel and it has the properties of a polyelectrolyte.

A gelled electrolyte was prepared (30% by weight of PANSSM, 35% of ethylene carbonate, 35% of propylene carbonate). This gel has good mechanical properties and a conductivity of $7.9 \times 10^{-4}$ S.cm$^{-1}$ at 30° C. The cationic transport number of this electrolyte was estimated to be 0.95. An electrochemical generator was prepared by utilizing said gelled electrolyte, a composite anode consisting of carbon coke, (80% by volume) mixed with the copolymer (PANSSM) as binder (20% by volume), and a composite cathode consisting of carbon black (6% by volume) LiCoO$_2$ (75% by volume) and a copolymer (PANSSM) (20% by volume).

This generator made it possible to do 1,000 cycles of charge/discharge between 3 and 4.2 V by maintaining a capacity higher than 80% of the capacity during the first cycle, when cycling at 25° C. It has very good performances during calls for power due to the utilization of fixed anions. The use of fixed anions has also permitted to improve the evolution of the interface resistance.

EXAMPLE 28

13.44 g (50 mmoles) of 1-dodecane-sulfonyl chloride C$_{12}$H$_{25}$SO$_2$Cl (commercially available from Lancaster) in solution in 30 ml of anhydrous tetrahydrofurane at –20° C. were treated with 8.8 g (100 mmoles) of sodium malononitrile. After 1 hour at 0° C., and 24 hours at room temperature, the solvent was evaporated and the product was reclaimed in 30 ml of water. The addition of 3.73 g (50 mmoles) of anhydrous potassium chloride KCl has enabled to obtain a precipitate which was recrystallized, and recovered by filtration and finally dried. The potassium salt of 1-dodecanesulfonylmalononitrile was obtained, in the form of a crystallized powder, having a purity determined by a proton and carbon RMN higher than 99%.

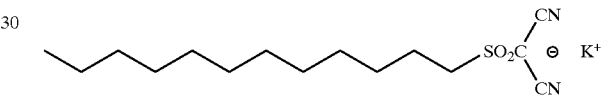

By a similar practice, the potassium salts of 1-butanesulfonylmalononitrile and 1-octylsulfonylmalononitrile were obtained respectively from 1-butanesulfonyl chloride and 1-octanesulfonyl chloride.

The lithium salts of these three derivatives were prepared in quantitative amounts by ionic exchange between the potassium salt and lithium chloride in anhydrous tetrahydrofurane.

The lithium salt of 1-dodecanesulfonylmalononitrile dissolved in a matrix of polyethylene oxide at a concentration O/Li=16/1 has a cationic transport number ≈0.55. The result is that when this compound is used in the electrolyte of a lithium battery with polymer electrolyte, the gradients of concentration which appear during the operation of the battery are substantially decreased. Performances during calls for power are thus improved.

The salts of 1-dodecanesulfonylmalononitrile had an undeniable interest as additives for laminating lithium and for the extrusion of polymers, in particular the extrusion of polyethylene oxide.

EXAMPLE 29

In 100 ml of water at 0° C., there is added 23.01 g (100 mmoles) of hexafluoropropanesultone (commercially available from Fluorchem). After 2 hours under stirring, the aqueous phase was extracted by means of two fractions of 20 ml of dichloromethane, and the organic phases were combined and dried with magnesium sulfate. After evaporation of dichloromethane and distillation of the collected liquid, there is obtained 16.94 g of 1-fluoro-2,2,2-trifluoroethanesulfonyl fluoride CF$_3$CHFSO$_2$F (yield: 94%;

purity, determined by a proton and fluorine RMN, higher than 99%).

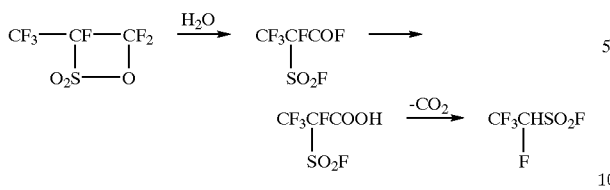

By operating in a glove box under argon, 9.2 g (50 mmoles) of the compound thus prepared were placed in solution in 10 ml of anhydrous tetrahydrofurane. After having brought this solution to −20° C., there is slowly added 50 ml of a 1 M solution (50 mmoles) in tetrahydrofurane of potassium tert-butoxide $(CH_3)_3COK$ (commercially available from Aldrich). After 15 min, 12.46 g (50 mmoles) of 1-bromododecane were added. The reaction is continued during 2 hours at −20° C., and during 24 hours at room temperature. There is then added 8.8 g (100 mmoles) of sodium malononitrile. After 48 hours, the solvent was evaporated and the residue was recrystallized in 50 ml of water containing 7.46 g (100 mmoles) of potassium chloride KCl. After filtration and drying, the potassium salt of 1-dodecane-2,2,2-trifluoroethanesulfonylmalononitrile was obtained, with a purity characterized by a proton, carbon and fluorine higher than 99%.

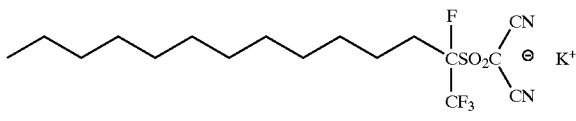

The lithium salt was obtained in quantitative yield by treating the potassium salt in anhydrous tetrahydrofurane with a stoichiometric quantity of anhydrous lithium chloride, filtration of the reaction mixture, evaporation of the solvent and drying under vacuum.

These compounds may be used as an additive for laminating lithium and for the extrusion of polymers, in particular the extrusion of polyethylene oxide.

They also have plasticizing and antistatic properties.

EXAMPLE 30

To 14.41 g (100 mmoles) of the sodium salt of 2-propenesulfonic acid $CH_2$=$CHCH_2SO_3Na$ in suspension in 60 ml of anhydrous acetonitrile at −20° C., there is added dropwise during 2 hours 11.9 g (100 mmoles) of thionyl chloride $SOCl_2$ diluted in 20 ml of benzene. After one night at −20° C., the reaction mixture was centrifuged to remove the sodium chloride formed and the solvents were evaporated by means of a rotary evaporator provided with a membrane pump. The liquid obtained was then distilled under vacuum in a short column to give 10.97 g of 2-propene-sulfonyl chloride $CH_2$=$CHCH_2SO_2Cl$ (yield 78%) characterized by a proton RMN. 7.03 g (50 mmoles) of this compound were then reacted under argon with 10.42 g (100 mmoles) of potassium malononitrile in 60 ml of anhydrous acetonitrile at −20° C. during 2 hours, and at room temperature during 24 hours. After evaporation of the solvent, the product was recrystallized in 15 ml of water. After filtration and drying, the potassium salt of 2-propenesulfonylmalononitrile was recovered, with a purity characterized by a proton and carbon RMN higher than 98%.

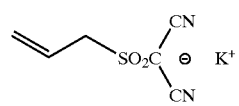

The lithium salt was obtained in quantitative yield by treating the potassium salt in anhydrous tetrahydrofurane with a stoichiometric quantity of anhydrous lithium chloride, filtration of the reaction mixture, evaporation of the solvent and drying under vacuum.

These salts may be used in chemical reactions where ethylenic bonds are involved. They may in particular be homo- or copolymerized by a polymerization which is initiated by free radical or by a coordinated polymerization catalyst, such as a zircanocene.

EXAMPLE 31

To 8.33 g of the potassium salt of 2-propene-sulfonylmalononitrile (40 mmoles), obtained according to Example 30, in 100 ml of water, there is added 6.9 g of 3-chloroperoxybenzoic acid (40 mmoles), obtained according to the procedure described by Scwartz & Blumbergs (J. Org. Chem., (1964), 1976). After 1 hour under strong stirring, the solvent was evaporated and the residue was recrystallized in 10 ml of ethanol. After filtration and drying, the potassium salt of 2,3-epoxypropene-1-sulfonylmalononitrile was recovered, with a purity characterized by a proton and carbon RMN higher than 98%.

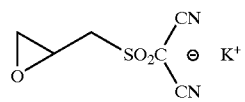

The lithium salt was obtained by treating the potassium salt in anhydrous tetrahydrofurane with a stoichiometric quantity of anhydrous lithium chloride, filtration of the reaction mixture, evaporation of the solvent and drying under vacuum.

These salts may be homo- or copolymerized by a polymerization initiated with anionic or cationic means. More generally, they may undergo chemical reactions in which oxetanes are involved.

The homopolymer of the potassium salt of 2,3-epoxybutane-1-sulfonylmalononitrile was prepared by a polymerization in tetrahydrofurane initiated by anionic means with potassium tert-butoxide, and the lithium polysalt was obtained by ionic exchange in THF with anhydrous lithium chloride. The latter has a conductivity in gelled medium (21% by weight of polyacrylonitrile, 38% of ethylene carbonate, 33% of propylene carbonate, 8% of homopolymer) of $1.2\times10^{-3}$ S.cm$^{-1}$ at 30° C. The cationic transport number in this electrolyte is 0.76. Moreover, this homopolymer is soluble in most of the usual organic solvents (tetrahydrofurane, acetonitrile, dimethylformamide, ethyl acetate, glymes, . . . ) and in aprotic solvating polymers.

EXAMPLE 32

50.74 (300 mmoles) of 2-amino-5-trifluoromethyl-1,3,4-thiadiazole (commercially available from Aldrich) were added under stirring to a mixture of 100 ml of concentrated hydrochloric acid and 30 ml of glacial acetic acid. The reaction mixture was brought to −10° C. and there is slowly added 22.42 g (325 mmoles) of sodium nitrite NaNO$_2$ in 35 ml of water. The diazotation reaction is continued for 1 hour. At the same time, a flow of sulfur dioxide SO$_2$ (commercially available from Fluka) in 300 ml of glacial acetic acid was passed through a fritted member until saturation. Then, there is added 7.5 g of copper(I) chloride CuCl and the addition of sulfur dioxide was continued until the color of the reaction mixture changed from yellow-green to blue-green. After having brought the reaction mixture to a temperature <10° C., during a period of 30 min, the previously prepared diazonium was added. A small amount of ether was added to decrease the quantity of foam which is formed after each addition. After the end of the addition of diazonium, the reaction mixture was poured into 1 liter of a mixture of water-ice (1:1). After melting of the ice, a yellow oil was separated in a decanting ampulla, and the aqueous phase was extracted with two fractions of 100 ml ether. After addition of the ether phase to the collected oil, the solution was washed with a concentrated solution of sodium bicarbonate until neutrality, then with water, and finally it was dried with magnesium sulfate. After evaporation of the solvent, there is recovered after distillation under vacuum 46.99 g of 2-sulfonyl-5-trifluoromethyl-1,3,4-thiadiazole chloride (62% yield) with a purity characterized by a proton and fluorine RMN higher than 98%.

Thereafter, by a process similar to the one described in Example 19, the lithium salt of 5-trifluoromethyl-1,3,4-thiadiazole-2-sulfonylmalononitrile was obtained, with a purity characterized by a carbon and fluorine RMN higher than 98%.

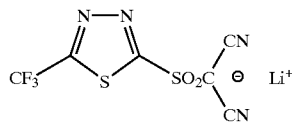

The potassium salt was obtained by treating the lithium salt, in a minimum amount of water, with potassium fluoride KF. After filtration, evaporation and drying, the potassium salt was recovered in quantitative yield.

These salts are soluble in most of the usual organic solvents (tetrahydrofurane, acetonitrile, dimethylformamide, ethyl acetate, glymes, . . . ) and in aprotic solvating polymers such as polyethylene oxide.

These salts have a potential of oxidation at a concentration 0.5 M in acetonitrile higher than 4.5 V towards a lithium anode. The lithium salt, alone or in admixture with the potassium salt, may be used for Li-Ion batteries with liquid or gel electrolytes, and polymer electrolyte lithium batteries.

A battery was assembled by utilizing an anode consisting of a mixture of carbon coke (80% by volume) and poly (vinylidene fluoride) (PVDF, commercially available from Montedison) as a binder (20% by volume), an electrolyte consisting of a mixture of ethylene carbonate and dimethylcarbonate (2:1), gelled with PVDF, containing the lithium salt of 5-trifluoromethyl-1,3,4-thiadiazole-2-sulfonylmalononitrile at a concentration 1 M and a composite cathode consisting of a mixture of carbon black (6% by volume), Li$_2$MnO$_4$ (75% by volume) and PVDF as binder (20% by volume). The battery was subjected to cycling at 25° C. After 1,000 cycles of charge/discharge between 2 and 4.7 V, the battery maintained a capacity representing about 50% of the capacity during the first cycle.

EXAMPLE 33

13.21 g (200 mmoles) of malononitrile were placed in solution in 150 ml of THF 15–20° C. There was then added, under argon, 44.87 g (400 mmoles) of DABCO and 21.18 g (200 mmoles) of cyanogene bromide BRCN. After 4 hours under stirring at −20° C., and 24 hours at room temperature, the reaction mixture was filtered to remove DABCO hydrochloride. There was then added 8.48 g of anhydrous lithium chloride (200 mmoles). After 24 hours under stirring, the reaction mixture was filtered to remove DABCO hydrochloride. After evaporation of the solvent and drying, 19 g (98% yield) of the lithium salt of tricyanomethane LiC(CN)$_3$ were recovered, with a purity characterized by a proton and carbon RMN higher than 98%.

The acid in ether solution was obtained, by adding 100 ml of hydrochloric acid 1 M at 0° C. (100 mmoles) to a suspension of 9.7 g of the lithium salt of tricyanaomethane (100 mmoles) in 30 ml of ether. After a few minutes under stirring, tricyanaomethane was recovered in the ether phase. After drying the organic phase with magnesium sulfate, 7.15 g of imidazole (105 mmoles) were added. A precipitate was immediately formed which was recovered by filtration and drying. 15.23 g (96% yield) of tricyanomethane imidazolium were recovered, with a purity characterized by a proton and carbon RMN higher than 99%.

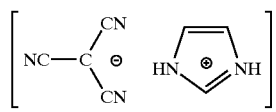

A crushing in a glove box of a molar mixture of 7 imidazoles for two salts of imidazolium has enabled to obtain a liquid in the mortar. This molten salt has a high protonic conductivity, higher than 10$^{-3}$ S.cm$^{-1}$ at 60° C. This molten salt may be used to prepare a polymer electrolyte, which is an anhydrous protonic conductor, by adding polyethylene oxide, preferably of high molecular weight or which could later on be cross-linked, to the molten salt without harming the conductivity. These polymer electrolytes are particularly interesting for preparing systems of modulating light such as electrochrome glazing including electrochrome systems with coloring material.

A polymer electrolyte made of the molten salt at 80% by weight and 20% by weight of polyethylene oxide of molecular weight 5×10$^6$ was used to prepare a membrane which is optically transparent in the visible range and has a good mechanical behaviour. Then, an electrochrome system was prepared in a glove box by utilizing this membrane enclosed between a first electrode consisting of the deposit on a glass plate of a layer of hydrogenated iridium oxide H$_x$IrO$_2$ and as a sub-conductive layer of tin oxide and a second electrode consisting of a layer of tungsten trioxide WO$_3$ and a conductive sub-layer of tin oxide. The electrochrome has permitted a variation of the optical absorption between 80% (discolored state) and 30%(colored state) and good performances in cycling (more than 20,000 cycles).

EXAMPLE 34

To 6.61 g of malononitrile (100 mmoles) in solution in 50 ml of THF at −20° C., there is added, in portions, 795 mg of lithium hydride LiH. After 2 hours at −20° C., there is added 20.14 g (100 mmoles) of 1-(trifluoromethanesulfonyl) imidazole) (commercially available from Fluka). The reaction was continued during 4 hours at −20° C., and during 48 hours at room temperature. The solvent was then evaporated and the residue was reclaimed in 60 ml of water. There is then added 14.66 g (100 mmoles) of 1-ethyl-3-methyl-1H-imidazolium chloride (commercially available from Aldrich) to the aqueous solution. A dense phase which is denser than water was immediately formed. This phase was recovered by extraction with dichloromethane. After evaporation of dichloromethane and drying under vacuum at 40° C. of the liquid obtained, a molten salt of 1-ethyl-3-methyl-1H-imidazolium of trifluoromethanesulfonylmalononitrile was obtained, with a purity characterized by a proton, carbon and fluorine RMN higher than 98%.

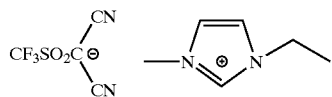

This molten salt has a conductivity of $4.5 \times 10^{-3}$ S.cm$^{-1}$ and a freezing point lower than $-20°$ C. Its wide range of redox stability makes it a particularly interesting electrolyte for electrochemical generators such as lithium batteries, supercapacitances, systems of light modulation, photovoltaic cells.

An electrochemical supercapacitance was prepared by utilizing the molten salt of 1-ethyl-3-methyl-1H-imidazolium of trifluoromethane-sulfonylmalononitrile as electrolyte and carbon/aluminum composites as electrodes. The electrodes of a thickness of 150 $\mu$m were placed on both sides of a microporous polyethylene having a thickness of 40 $\mu$m and the complete system was sealed in a glove box in a housing of button shaped battery after having been soaked with the molten liquid salt. The supercapacity obtained has enabled to produce more than 100,000 cycles of charge/discharge between 0 and 2.5 V for a density of energy higher than 25 Wh/l and a delivered power higher than 1,500 W/l.

EXAMPLE 35

In 30 ml of THF, 6.76 g (40 mmoles) of pentafluoropyridine (commercially available from Aldrich) were reacted with 4.17 g (40 mmoles) of potassium malononitrile KHC(CN)$_2$ in the presence of 4.49 g (40 mmoles) of DABCO. After 48 hours under stirring, the solvent was evaporated and the residue was recrystallized in 15 ml of water to which 4 g of potassium chloride has been added. After filtration and drying, there is obtained 5.29 g of the potassium salt of 4-malononitrile-pentafluoropyridine (73% yield), with a purity determined by a carbon RMN higher than 99%.

According to the same process, the potassium salt of 2-malononitrile-3,5-dinitrobenzo-trifluoride was prepared from 10.82 g (40 mmoles) of 2-chloro-3,5-dinitrobenzotrifluoride (commercially available from Aldrich), with a purity determined by a fluorine, proton and carbon RMN higher than 99%.

The lithium salts were obtained by ionic exchange with lithium chloride in THF.

These salts are soluble in most of the usual organic solvent (tetrahydrofurane, acetonitrile, dimethylformamide, ethyl acetate, glymes, . . . ) and in aprotic solvating polymers.

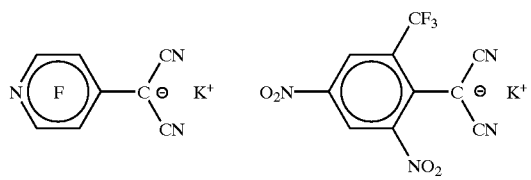

These examples illustrate the grafting of the anion of malononitrile on an aromatic nucleus containing substituents which are activated by the presence of electroattractor groups and/or heteroatoms in the aromatic cycle.

EXAMPLE 36

In a three-neck flask provided with a cooler, a mechanical stirrer and a neutral gas inlet (Argon), there is introduced 9.5 g of a copolymer of dimethylsiloxane and (hydrogen) (methyl)-siloxane (HMS 301 25% SiH, M$_w$ 1900, commercially available from Gelest Inc., Tullytown, Pa., USA) in solution in tetrahydrofurane. There is then added 6.04 g of the lithium salt of vinylsulfonylmalononitrile and 70 mg of chloroplatinic acid H$_2$PtCl$_6$. The mixture was heated to reflux during four hours. The polymer was then reprecipitated in ethanol.

There is thus obtained a copolymer of dimethylsiloxane and of the lithium salt of (ethyl-sulfonylmalononitrile) (methyl)-sixolane which is soluble in most of the organic solvents, including in amounts >2% in oils or silicon materials, to which they give antistatic properties.

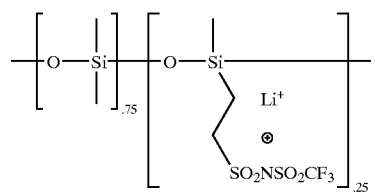

EXAMPLE 37

By a process similar to the one described in Example 28, the potassium salt of (1R)-(−)-10-camphorsulfonylmalononitrile was obtained from (1R)-(−)-10-camphorsulfonyl chloride (commercially available from Aldrich) and the potassium salt of (1S)-(+)-camphorsulfonylmalononitrile was obtained from (1S)-(+)-10-camphorsulfonyl (commercially available from Aldrich) with yields higher than 70% and a purity, determined by a proton and carbon RMN higher than 99%.

The corresponding lithium salts were obtained by ionic exchange (metathesis) in tetrahydrofurane with lithium chloride.

Scandium salts were obtained by treating the corresponding potassium salts with a stoichiometric quantity of scandium tetrafluoroborate (BF$_4$)$_3$ in acetonitrile. After filtration to remove the precipitate of potassium tetrafluoroborate KBF$_4$ and evaporation of the solvent, scandium salts of the two enantiomers were recovered in quantitative yield.

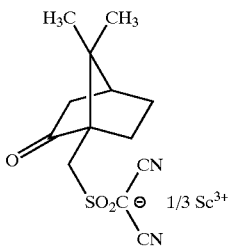 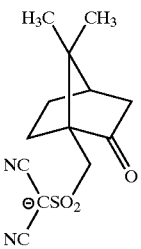 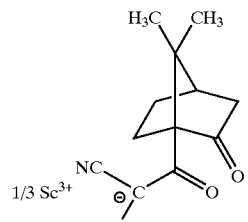

These salts are soluble in most of the polar organic solvents (acetonitrile, tetrahydrofurane, DMF, . . . ) and in aprotic solvating polymers.

EXAMPLE 38

The two enantiomers of the lithium salt of (N-methoxybutyl-N-2-butyl-34-methyl)aminosulfonylmalononitrile were obtained by a process, similar to the one described in Example 14, from the two enantiomers of N-methoxybutyl-N-2-butyl-3-methyl-amine (commercially available from Air Products) with a purity higher than 97%.

The potassium salts were obtained by treating the lithium salts with potassium fluoride KF in water. After filtration, evaporation and drying, the potassium salts were recovered in quantitative yield.

The scandium salts were obtained by treating the potassium salts with a stoichiometric quantity of scandium tetrafluoroborate $Sc(BF_4)_3$ in acetonitrile. After filtration to eliminate the precipitate of tetrafluoroborate $KBF_4$ and evaporation of the solvent, the scandium salts of the two enantiomers were recovered in quantitative yield.

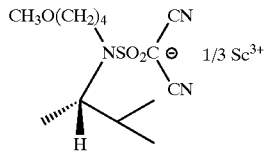 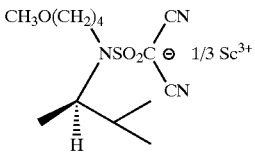

These salts are soluble in most of the polar organic solvents (acetonitrile, tetrahydrofurane, DMF, . . . ) and in aprotic solvating polymers

EXAMPLE 39

1.82 g (10 mmoles) of (1S)-(+)-ketopinic acid (commercially available from Aldrich) were placed in solution in 10 ml of pyridine and there is added 1.04 g (10 mmoles) of the potassium salt of malononitrile and 2.06 g (10 mmoles) of dicyclohexylcarbodiimide. After 48 hours under stirring, the mixture was filtered to remove dicyclohexylurea. After evaporation of the filtrate, the potassium salt of (1S)-(+)-ketopinic-acetylmalononitrile was obtained, with a purity determined by a proton and carbon RMN higher than 97%.

The scandium salt was obtained by treating the potassium salt with a stoichiometric quantity of scandium tetrafluoroborate $Sc(BF_4)_3$ in acetonitrile. After filtration to remove the precipitate of potassium tetrafluoroborate $KBF_4$ and evaporation of the solvent, the scandium salt of (1S)-(+)-ketopinic-acetylmalononitrile was recovered in quantitative yield.

EXAMPLE 40

Catalysis of an Aldol Condensation

The scandium salt of dibutylaminosulfonylmalononitrile was obtained by treating the potassium salt, obtained in Example 14, with a stoichiometric quantity of scandium tetrafluoroborate $Sc(BF_4)_3$ in acetonitrile. After filtration to eliminate the precipitate of potassium tetrafluoroborate $KBF_4$ and evaporation of the solvent, the scandium salt of dibutylaminosulfonylmalononitrile $Sc(DBSM)_3$ was recovered in quantitative yield.

This salt was used as catalyst for a reaction of aldol condensation in the following manner: To a solution containing 32.6 mg (0.04 mmoles) of the scandium salt of dibutylaminosulfonylmalononitrile (10% molar) in 1.5 ml of dichloromethane, there is added a mixture of 105 mg (0.6 mmoles) of 1-ene-2-methyl-1-silylacetal-1-methoxypropene $(CH_3)_2C=C(OSiMe_3)OMe$ and 42 mg (0.4 mmoles) of benzaldehide in 1 ml of dichloromethane. After 16 hours under stirring at room temperature, water is added and the product was extracted with dichloromethane. the organic phase was washed with three fractions of 10 ml of water, and dichloromethane was evaporated. The residue was then treated with a tetrahydrofurane/HCl 1 M (10:1) during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of the solvents, the raw product was chromatographed on silica gel. Methyl-3-hydroxy-2,2-dimethyl-phenylpropionate was obtained with a yield of 89%.

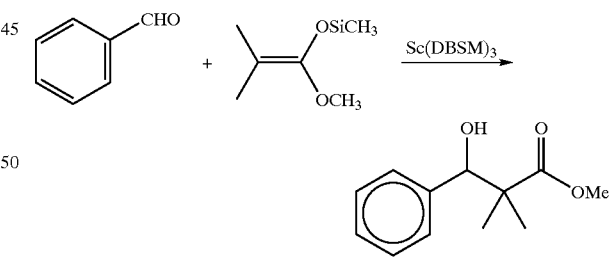

The same reaction was carried out with a quantity of catalyst divided into about 10, without any decrease of the yield of the compound methyl-3-hydroxy-2,2-dimethyl-phenylpropionate. This result is due to the good solubility in dichloromethane of the scandium salt of dibutylaminosulfonylmalononitrile.

EXAMPLE 41

Catalysis of Michael Addition

The scandium salt of dibutylaminosulfonylmalononitrile, obtained in Example 40, was used at catalyst in a Michael addition in the following manner.

To a solution of 32.6 mg (0.04 mmoles) of the scandium salt of dibutylaminosulfonylmalononitrile (10% molar) in 1.5 ml of dichloromethane, there is added a mixture of 105 mg (0.6 mmoles) of 1-ene-2-methyl-1-silylacetal-1-methoxypropene $(CH_3)_2C=C(OSiMe_3)OMe$ and 84 mg (0.4 mmoles) of chalcon in 1 ml of dichloromethane. After 12 hours under stirring at room temperature, water is added and the product was extracted with dichloromethane. The organic phase was washed with three fractions of 10 ml of water. and dichloromethane was evaporated. The residue was then treated with a tetrahydrofurane/HCl 1 M (20:1) mixture during 0.5 hours at 0° C. After diluting with hexane, a saturated solution of sodium bicarbonate was added, and the product was extracted with dichloromethane. The organic phase was washed with a saturated solution of sodium chloride, and dried with sodium sulfate. After evaporation of these solvents, the raw product was chromatographed on silica gel. The 1,5-dicarbonylated compound was obtained with a yield of 87%.

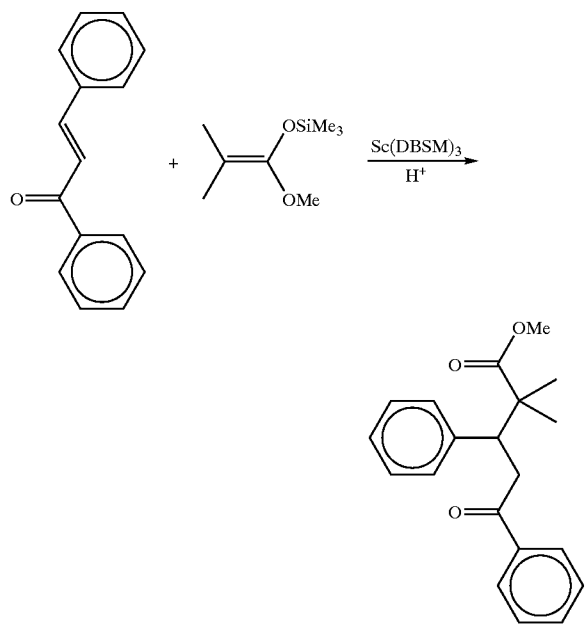

The same reaction was carried out with a quantity of catalysts divided about in 10, without a decrease of the yield of the 1,5-dicarbonylated compound. This result is due to the good solubility in dichloromethane of the scandium salt of dibutylaminosulfonylmalononitrile.

EXAMPLE 42

Catalysis of a Friedel-Crafts Reaction

The scandium salt of dibutylaminosulfonylmalononitrile, obtained in Example 40, was used as catalyst in a Friedel-Crafts reaction of acylation, by operating in the following manner. In 40 ml of anhydrous nitromethane, there is added 570 mg (700 μmoles) of $Sc(DBSM)_3$, and 1.08 g (10 mmoles) of anisol and 2.04 g of acetic anhydride. After stirring during 10 min at 21° C., the reaction mixture was diluted with 50 ml of ether and the reaction was inhibited by using 100 ml of a saturated solution of sodium bicarbonate $NaHCO_3$. After filtration on Celite, the solution was extracted with three fractions of 50 ml of ether, and the collected ether phase was washed with a saturated solution of potassium chloride. After drying the ether phase with magnesium sulfate and evaporation, 1.46 g of p-methoxyacetophenone (97% yield) was recovered, with a purity characterized by a proton RMN higher than 99%.

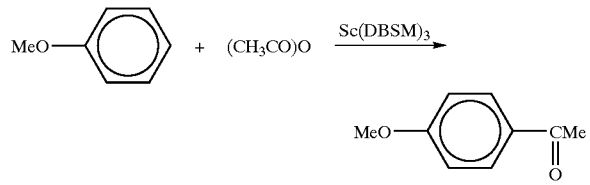

It is thus confirmed that the scandium salt of dibutylaminosulfonylmalononitrile is a very good catalyst for Friedel-Crafts reactions of acylation.

EXAMPLE 43

Catalysis of a Diels-Alder Reaction

The scandium salt of (1S)-(+)-ketopinic-acetylmalononitrile (ScKAM), prepared according to Example 39, the scandium salt of (1R)-(−)-10-camphorsulfonylmalononitrile (ScCSM), prepared according to Example 37, and the scandium salt of (N-methoxybutyl-N-2-butyl-3-methyl)aminosulfonyl-malononitrile(ScMBBMASM), prepared according to Example 38, were used as catalysts of a Diels-Alder reaction, enabling a reaction of a methylvinylketone with cyclopentadiene.

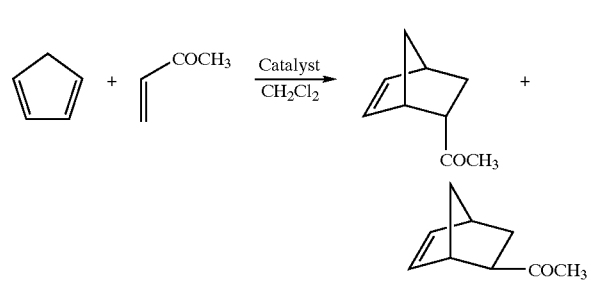

For each of the scandium salts mentioned above, the following operating procedure was followed.

To a solution of 651 mg (10 mmoles) of freshly distilled cyclopentadiene and 701 mg (10 mmoles) of methylvinylketone in 10 ml of dichloromethane, there is added 200 μmoles of the salt of scandium chiral. After 24 hours at room temperature, the reaction mixture was filtered to remove the catalysis suspension. In all cases, there is obtained a reaction yield, determined by chromatography in aqueous phase higher than 90%. After separation of the different products of the reaction on a chiral column, the enantiomeric excesses were determined by RMN. The results, which show the efficiency of the salts for a chiral catalysis, are given in the following table.

| Chiral Catalyst | Enantiomeric excess |
|---|---|
| ScKAM | 61% |
| ScCSM | 78% |
| ScMBBMASM | 70% |

EXAMPLE 44

To 18.11 g (100 mmoles) of 6-bromo-1-hexanol and 11.22 g (100 mmoles) of DABCO in 100 ml of anhydrous THF at −20° C., there is slowly added 19.06 g (100 mmoles) of tosyl chloride. After 24 hours under stirring at −20° C., the reaction mixture was filtered to remove the precipitate of DABCO hydrochloride. After evaporation of the solvent, a quantitative amount of 6-bromo-1-hexanol tosylate $CH_3FSO_2O(CH_2)_6Br$ was recovered. This compound was thereafter dissolved in 20 ml of THF with 40 g of aniline $FNH_2$ (200 mmoles) and this solution was heated to reflux overnight. After cooling, 300 ml of water were added and the organic phase was extracted with ether. After washing with water, the ether phase was dried with magnesium sulfate. After evaporation and drying, 23 g of N-(6-bromohexyl) aniline was obtained.

By operating in a glove box under argon, 9.2 g of 1-fluoro-2,2,2-trifluoroethanesulfonyl $CF_3CHFSO_2F$ (50 mmoles), prepared according to Example 29, were placed in solution in 10 ml of anhydrous tetrahydrofurane. After bringing the temperature of this solution to −20° C., there is slowly added 50 ml of a 1 M solution in tetrahydrofurane of potassium tert-butoxide $(CH_3)_3COK$ (commercially available from Aldrich). After 15 min, 12.81 (50 mmoles) of N-(6-bromohexyl)aniline were added. The reaction was continued during 2 hours at −20° C., and during 24 hours at room temperature. 8.8 g (50 mmoles) of sodium malononitrile and 5.61 g of DABCO were then added. After 48 hours, the reaction mixture was filtered to remove the precipitate of DABCO hydrochloride, and the solvent was evaporated and the residue was recrystallized in 50 ml of water containing 7.46 (100 mmoles) of potassium chloride KCl. After filtering and drying, the potassium salt of 1-(6-anilino-1-hexane)-2,2,2-trifluoroethanesulfonylmalononitrile was obtained, with a purity characterized by a proton, carbon and fluorine RMN higher than 99%.

8.87 g of this compound (20 mmoles) were thereafter dissolved in 200 ml of a 1 M solution of hydrochloric acid and there is slowly added, during a period of 3 hours, 4.56 g (20 mmoles) of ammonium persulfate $(NH_4)_2S_2O_8$. The reaction is continued during 14 hours. The reaction mixture was then neutralized with potassium hydroxide, and concentrated to a volume of ≈40 ml. After filtration and drying, 5.9 g of a black powder of the following compound were recovered:

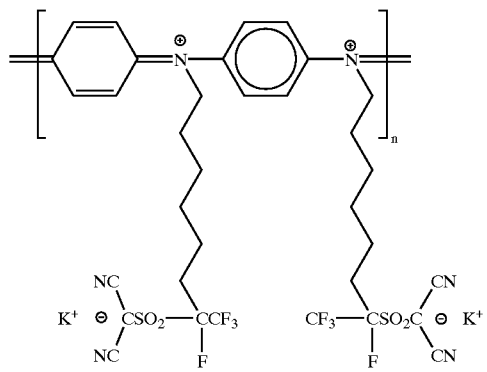

This polymer compound which comprises a doping anion very delocalized in its structure presents properties of electronic conductor (PCE). The low basic character of this anion improves the stability of the polymer. In humid medium, this conductivity determined by a four point measurement is initially of is the order of 4 $S.cm^{-1}$.

This material was tested as the cathode of a battery. The battery had the following structure:

a composite cathode consisting of 40% by volume of the polymer compound obtained in the present example and 60% by volume of polyethylene oxide of molecular weight $3 \times 10^5$;

an electrolyte consisting of a film of polyethylene oxide of molecular weight $5 \times 10^6$ containing the lithium salt of butanesulfonylmalononitrile, obtained in Example 28, at a concentration O/Li=20/1;

a metallic lithium anode.

After mounting the assembly in a housing for a button shaped battery, the battery obtained was cycled at a temperature of 60° C. between 3 V and 3.9 V. It was possible to make more than 1,000 cycles of charge/discharge while keeping 80% of the capacity of the first cycle.

In addition, the polymer compound of the present example is a good corrosion inhibitor of ferrous metals and enables to produce deposits on plastic materials treated by Corona effect.

EXAMPLE 45

To 11.8 g (0.1 mole) of methyl oxalate in 30 ml of THF 20.8 g (0.2 moles) of potassium malononitrile in solution in 80 ml of THF were added. A precipitate was formed in a few minutes. The mixture was kept under stirring in a neutral atmosphere during 2 hours, and it was filtered and washed with two portions of 50 ml ether. The potassium salt of the following anion was obtained, in the form of a beige solid:

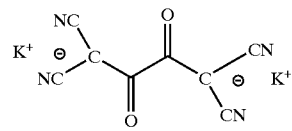

This compound forms anionic complexes with metals such as aluminum, zinc, magnesium, iron, chromium. These complexes are soluble in aprotic solvents or solvating polymers and are useful as vehicular carriers of complexed metals (Mg, Al) or as stable redox couple (Fe, Cr).

EXAMPLE 46

To 1.98 g (10 mmoles) of sulfonyldiimidazole in 10 ml of acetonitrile there is added 1.42 g (20 mmoles) of sodium malononitrile in solution in 20 ml ether. A precipitate is immediately formed. The mixture was kept under stirring in a neutral atmosphere during 2 hours, and it was filtered and washed with the two portions of 20 ml ether. The lithium salt of the following anion was obtained in the form of a white solid:

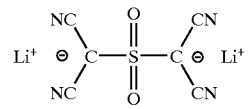

This salt is soluble in polar solvents, such as propylene carbonate or solvating polymers based on ethylene oxide, and gives conductivities of the order of $10^{-4}$ $S.cm^{-1}$ at 90° C. with an excellent stability of the interface with lithium.

EXAMPLE 47

The lithium salt of trifluoromethanesulfonylmalononitrile obtained in Example 2 and the lithium polysalt of 2,3-epoxypropane-1-sulfonylmalononitrile obtained in Example 31 was tested in electrochemical generators according to the lithium-polymer technology.

For each salt, a battery was prepared by superposing the following layers:

- a current collector of stainless steel with a thickness of 2 mm;
- a cathode consisting of a pastil of a film of composite material having a thickness of 72 μm of vanadium dioxide (45% by volume), Shawinigan black (5% by volume) and a polyethylene oxide of molecular weight $M_w=3\times10^5$ (50% by volume);
- an electrolyte consisting of a pastil of a film of polyethyleneoxide of molecular weight $M_w=5\times10^6$ containing one of the two lithium salts at a concentration O/Li= 15/1;
- an anode consisting of a sheet of metallic lithium having a thickness of 50 μm;
- a current collector similar to the above collector.

The pastils constituting the electrode and the electrolyte were cut out in a glove box and piled in the order indicated above.

The collectors were thereafter placed on both sides of the battery obtained.

The assembly was sealed in a housing for button shaped battery which enables to protect the generator from the atmosphere and also to exercise a mechanical stress on the films. The battery was then placed in an enclosure under argon mounted in a drying oven at a temperature of 60° C. It was thereafter cycled between 1.8 and 3.3 V at a rate of charge and discharge of C/10 (nominal capacity charged or discharged in 10 hours).

The curves of cycling obtained are represented in FIG. 1 (salt of lithium of trifluoromethanesulfonylmalononitrile: Curve A; polysalt of lithium of 2,3-epoxypropane-1-sulfonyl-malononitrile: Curve B) On this figure, the use, U, expressed in % is given in ordinate, and the number of cycles C is given in abscissae.

What is claimed is:

1. Ionically conductive material comprising an ionic compound in solution in a solvent, wherein the ionic compound is derived from malononitrile and comprises an anionic part and sufficient cationic parts $M^{m+}$ to provide electronic neutrality to the ionic compound, characterized in that M is an hydroxonium, a nitrosonium $NO^+$, an ammonium $-NH_4^+$, a metallic cation having a valency m, an onium cation having a valency m or an organometallic cation having a valency m, and that the anionic part corresponds to one of the formula $R_D-Y-C(C\equiv N)_2^-$ or $Z-C(C\equiv N)_2$ in which:

A) Z represents an electroattractor radical having a Hammett parameter at least equal to that of a phenyl radical, selected from:
  i) $-CN$, $-NO_2$, $-SCN$, $-N_3$, $FSO_2-$, $-CF_3$, $R'_FCH_2-$, fluoroalkyloxy, fluoroalkylthioxy, fluoroalkenyloxy, fluoroalkenylthioxy radicals, wherein $R'_F$ is a perfluorinated radical;
  ii) radicals comprising one or more aromatic nuclei optionally containing at least one nitrogen, oxygen, sulfur or phosphorus atom, said nuclei optionally being selected from condensed nuclei and nuclei optionally carrying at least one substituent selected from halogens, $-CN$, $-NO_2$, $-SCN$, $-N_3$, $CF_2=CF-O-$, radicals, $R_F-$ and $R_FCH_2-$ in which $R_F$ is a perfluoroalkyl alkyl having 1 to 12 carbon atoms, fluoroalkyloxy groups, fluoroalkylthioxy groups, alkyl, alkenyl, oxa-alkyl, oxa-alkenyl, aza-alkyl, aza-alkenyl, thia-alkyl, and thia-alkenyl radicals, polymer radicals, radicals having at least one ionophorous group selected from cationic, anionic, and both;
  with the proviso that one substituent Z may be a monovalent radical, a multivalent radical, or part of a multivalent radical or a dendrimer carrying at least one $-C(C\equiv N)_2$ group, or a polymer radical;

B) Y represents a carbonyl group, a thiocarbonyl group, a sulfonyl group, a sulfinyl group or a phosphonyl group and:

C) $R_D$ is a radical selected from
  a) $R_v$, wherein $R_v$ is selected from alkyl or alkenyl radicals, aryl, arylalkyl, alkylaryl or alkenylaryl radicals, alicyclic, heterocyclic, or polycyclic radicals;
  b) $R_w$, wherein $R_w$ is selected from alkyl or alkenyl radicals comprising at least one functional ether, thioether, amine, imine, amide, carboxyl, carbonyl, isocyanate, isothiocyanate, hydroxy;
  c) $R_x$, wherein $R_x$ is selected from aryl, arylalkyl, arylalkenyl, alkylaryl or alkenylaryl radicals, in which one or more of the aromatic nuclei and the substituents of the nucleus comprises a heteroatom;
  d) $R_y$, wherein $R_y$ is selected from radicals comprising condensed aromatic cycles which optionally comprise at least one heteroatom selected from nitrogen, oxygen, sulfur;
  e) $R_z$, wherein $R_z$ is selected from halogenated or perhalogenated alkyl, alkenyl, aryl, arylalkyl, alkylaryl radicals, said radicals optionally comprising fuctional ether, thioether, imine, amine, carboxyl, carbonyl or hydroxy groups;
  f) radicals $R_CC(R')(R'')-O-$ in which $R_C$ is an alkyl perfluorinated radical and R' and R" are independently selected from an hydrogen atom or a radical selected from $R_v$, $R_w$, $R_x$, and $R_y$;
  g) radicals $(R_B)_2N-$, in which the radicals $R_B$ are independently selected from $R_v$, $R_w$, $R_x$, $R_y$, and $R_z$, one of the $R_B$ is a halogen atom, or the two radicals $R_B$ together form a divalent radical, wherein when the two radicals $R_B$ form a divalent radical, $(R_B)_2N-$ is a cycle;
  h) polymer radicals,
  i) radicals having one or more ionophorous groups selected from cationic and anionic groups;
  with the proviso that one substituent $R_D$ may be a monovalent radical, part of a multivalent radical carrying a plurality of $-Y-C^-(C\equiv N)_2$ groups or a polymer radical;
  with the proviso that when Y is a carbonyl and $R_D$ is a perfluoroalkyl radical having 1 to 3 carbon atoms, or when Z is $-CN$, M is different from an alkali metal.

2. Ionically conductive material according to claim 1, characterized in that the organic cation is an onium cation selected from the group consisting of $R_3O^+$, $NR_4^+$, $RC(NHR_2)_2^+$, $C(NHR_2)_3^+$, $C_5R_6N^+$, $C_3R_5N_2^+$, $C_3R_7N_2^+$, $C_2R_4N_3^+$, $SR_3^+$, $PR_4^+$, $IR_2^+$, $(C_6R_5)_3C^+$ cations, the radicals R independently selected from H and a radical selected from the group consisting of:
  a) alkyl, alkenyl, oxa-alkyl, oxa-alkenyl, aza-alkyl, aza-alkenyl, thia-alkyl, thia-alkenyl, aryl, arylalkyl, alkylaryl, alkenylaryl radicals, dialkylamino radicals and dialkylazo radicals;
  b) cyclic or heterocyclic radicals optionally comprising at least one lateral chain comprising heteroatoms such as nitrogen, oxygen, sulfur;

c) cyclic or heterocyclic radicals optionally comprising heteroatoms in the aromatic nucleus;
d) groups comprising a plurality of aromatic or heterocyclic nuclei, condensed or non-condensed, optionally containing at least one nitrogen, oxygen, sulfur or phosphorus atom;

with the proviso that a plurality of radicals R optionally together form aliphatic or aromatic cycles, optionally enclosing the center carrying the cationic charge.

3. Ionically conductive material according to claim 2, characterized in that the onium cation is part of the radical Z or the radical $R_D$.

4. Ionically conductive material according to claim 2, characterized in that the onium cation is part of a recurring unit of a polymer.

5. Ionically conductive material according to claims 2, characterized in that the cation $M^+$ is a cationic heterocycle with aromatic character, including at least one nitrogen atom which is alkylated in the cycle.

6. Ionically conductive material according to claim 5, characterized in that the cation is a substituted or unsubstituted imidazolium, triazolium, pyridinium, or 4-dimethyl-amino-pyridinium.

7. Ionically conductive material according to claim 2, characterized in that the cation M is a group having a bond —N≡N, —N≡N$^+$, a sulfonium group, an iodonium group, or an arene-ferrocenium cation, which is substituted or non-substituted, optionally incorporated in a polymeric network.

8. Ionically conductive material according to claim 2, characterized in that the cation is a diaryliodonium cation, a dialkylaryliodonium cation, a triarylsulfonium cation, a trialkylaryl sulfonium cation, or a substituted or non-substituted phenacyl-dialkyl sulfonium cation.

9. Ionically conductive material according to claim 2, characterized in that the aryliodonium cation, or the alkylaryliodonium cation, or the triarylsulfonium cation, or the alkylaryl sulfonium cation, or the phenacyl-dialkyl sulfonium cation are part of a polymer chain.

10. Ionically conductive material according to claim 2, characterized in that M is an organic cation incorporating a group 2,2'[azobis(2-2'-imidazolinio-2-yl)propane]$^{2+}$ or 2,2'-azobis(2-amidiniopropane)$^{2+}$.

11. Ionically conductive material according to claim 1, characterized in that the cation M is a metallic cation selected from the group consisting of cations of alkali metals, cations of alkaline-earth metals, cations of transition metals, cations of trivalent metals and cations of rare earths.

12. Ionically conductive material according to claim 1, characterized in that the cation is a metallocenium, selected from the group consisting of cations derived from ferrocene, titanocene and zirconocene, indenocenium cations, arene metallocenium cations, cations of transition metals complexed with ligands optionally having a chirality and organometallic cations having one or more alkyl or alyl groups covalently bound to an atom or a group of atoms, said cations optionally being part of a polymer chain.

13. Ionically conductive material according to claim 1, characterized in that the substituent Z is selected from the group consisting of —OC$_n$F$_{2n+1}$, —OC$_2$F$_4$H, —SC$_n$F$_{2n+1}$ and —SC$_2$F$_4$H, —OCF=CF$_2$, —SCF=CF$_2$, n being a whole number from 1 to 8.

14. Ionically conductive material according to claim 1, characterized in that Z is a radical C$_n$F$_{2n+1}$CH$_2$—, n being a whole number from 1 to 8.

15. Ionically conductive material according to claim 1, characterized in that $R_D$ is a radical selected from alkyl, alkenyl, oxa-alkyl, oxa-alkenyl, aza-alkyl, aza-alkenyl, thia-alkyl or thia-alkenyl having 1 to 24 carbon atoms, or from aryl, arylalkyl, alkylaryl or alkenylaryl having 5 to 24 carbon atoms.

16. Ionically conductive material according to claim 1, characterized in that $R_D$ is a radical selected from alkyl or alkenyl radicals having 1 to 12 carbon atoms and optionally comprising one or more members of at least one heteroatom O, N or S in the main chain or in a lateral chain, a hydroxy group, a carbonyl group, an amino group, and a carboxyl group.

17. Ionically conductive material according to claim 1, characterized in that $R_D$ is part of a poly(oxyalkylene) radical or a polystyrene radical.

18. Ionically conductive material according to claim 1, characterized in that $R_D$ is a radical having an iodonium, sulfonium, oxonium, ammonium, amidinium, guanidinium, pyridinium, imidazolium, triazolium, phosphonium or carbonium, said ionic group behaving totally or partially as cation $M^+$.

19. Ionically conductive material according to claim 1, characterized in that $R_D$ has one or more anionic ionophorous groups consisting of a carboxylic function (—CO$_2^-$), a sulfonic function (—SO$_3^-$), a sulfonimide function (—SO$_2$NSO$_2$—) or a sulfonamide function (—SO$_2$N—).

20. Ionically conductive material according to claim 1, characterized in that $R_D$ includes one ore more groups selected from an ethylenic unsaturation group, a condensable group and a group which is dissociable by thermal means, by photochemical means or by ionic dissociation.

21. Ionically conductive material according to claim 1, characterized in that $R_D$ represents a chromophore group or a self-doped electronically conductive polymer or a hydrolysable alkoxysilane.

22. Ionically conductive material according to claim 1, characterized in that $R_D$ represents a recurring unit or a polymer chain.

23. Ionically conductive material according to claim 1, characterized in that $R_D$ includes a group capable of trapping free radicals.

24. Ionically conductive material according to claim 1, characterized in that $R_D$ is a dissociating dipole.

25. Ionically conductive material according to claim 1, characterized in that $R_D$ includes a disulfide, a thioamide a ferrocene, a phenothiazine, a bis(dialkylaminaryl), a nitroxyde, or an aromatic imide.

26. Ionically conductive material according to claim 1, characterized in that $R_D$ is a complexing ligand.

27. Ionically conductive material according to claim 1, characterized in that $R_D$—Y— is an amino acid, or a biologically active polypeptide.

28. Ionically conductive material according to claim 1, characterized in that $R_D$ represents a radical having a valency v higher than 2 and includes a —C(C≡N)$_2^-$ at both free ends.

29. Ionically conductive material comprising an ionic compound in solution in a solvent, characterized in that the ionic compound is a compound according to claim 1.

30. Ionically conductive material according to claim 29, characterized in that the cation of the ionic compound is ammonium, or a cation derived from a metal, or an organic cation selected from a substituted ammonium, a imidazolium, a triazolium, a pyridinium, a 4-dimethylamino-pyridinium, said cation optionally carrying a substituent on the carbon atoms of the cycle.

31. Ionically conductive material according to claim 29, characterized in that the substituent $R_D$ of the ionic compound comprises an alkyl group, an aryl group, an alkylaryl group or an arylalkyl group; a mesomorphous group or a group comprising at least one group selected from an ethylenic unsaturation, a condensable group, and a group which is dissociable by thermal means, by photochemical means or by ionic dissociation; a self-doped electronically conductive polymer; a hydrolyzable alkoxysilane, a free radical trap; a dissociating dipole; a redox couple; a complexing ligand.

32. Ionically conductive material according to claim 29, characterized in that the substituent $R_D$ of the ionic compound is an alkyl or alkenyl which contains at least one heteroatom selected from O, N or S; an alkyl or an alkenyl carrying a hydroxy group, a carbonyl group, an amino group, a carboxyl group, an aryl, an arylalkyl, an alkylaryl or an alkenylaryl in which the lateral chains, the aromatic nuclei, or both comprise heteroatoms.

33. Material according to claim 29, characterized in that the substituent $R_D$ is a recurring unit of a polymer.

34. Ionically conductive material according to claim 29, characterized in that the substituent Z of the ionic compound is selected from the group consisting of $-OC_nF_{2n}+1$, $-OC_2F_4H$, $-SC_nF_{2n}+1$, $-SC_2F_4H$, $-OCF=CF_2$, and $-SCF=CF_2$.

35. Ionically conductive material according to claim 29, characterized in that the solvent is either an aprotic liquid solvent, selected from linear ethers and cyclic ethers, esters, nitriles, nitro derivatives, amides, sulfones, sulfolanes, sulfamides and partially halogenated hydrocarbons, or a polar polymer, or a mixture thereof.

36. Ionically conductive material according to claim 35, characterized in that the solvent is a solvating polymer, cross-linked or non-cross-linked, which may carry grafted ionic groups.

37. Ionically conductive material according to claim 36, characterized in that the solvating polymer is selected from polyethers of linear structure, comb or blocks, which may form a network, based on poly(ethylene oxide), copolymers containing the ethylene oxide or propylene oxide or allylglycidylether unit, polyphosphazene, cross-linked networks based on polyethylene glycol cross-linked with isocyanates, networks obtained by polycondensation and carrying groups enabling the incorporation of cross-linkable groups and block copolymers in which some blocks carry functions which have redox properties.

38. Ionically conductive material according to claim 29, characterized in that the solvent consists essentially of an aprotic liquid solvent and a polar polymer solvent comprising units containing at least one heteroatom selected from sulfur, oxygen, nitrogen and fluorine.

39. Ionically conductive material according to claim 38, characterized in that the polar polymer mainly contains units derived from acrylonitrile, vinylidene fluoride, N-vinylpyrrolidone or methyl methacrylate.

40. Ionically conductive material according to claim 29, characterized in that it additionally contains at least an ionic salt.

41. Ionically conductive material according to claim 29, characterized in that it additionally contains a mineral or organic in the form of powder or fibres.

42. Electronically conductive material, characterized in that it comprises an ionic compound according to claim 1.

43. Electronically conductive material according to claim 42, characterized in that the cationic part of the ionic compound is a polycation consisting of a doped "p" conjugated polymer.

44. Electronically conductive material according to claim 43, characterized in that the substituent Z of the ionic compound comprises an alkyl chain having 6 to 20 carbon atoms.

45. Ionically conductive material according to claim 1, characterized in that the substituent $R_D$ of the ionic compound is an alkyl or alkenyl which contains at least one heteroatom selected from O, N or S; an alkyl or an alkenyl carrying a hydroxy group, a carbonyl group, an amino group, a carboxyl group, an aryl, an arylalkyl, an alkylaryl or an alkenylaryl in which the lateral chains, the aromatic nuclei, or both comprise heteroatoms.

46. Ionically conductive material according to claim 1, characterized in that the substituent $R_D$ is a recurring unit of a polymer.

47. Ionically conductive material according to claim 1, characterized in that the solvent is either an aprotic liquid solvent, selected from linear ethers and cyclic ethers, esters, nitrites, nitro derivatives, amides, sulfones, sulfolanes, sulfamides and partially halogenated hydrocarbons, or a polar polymer, or a mixture thereof.

48. Ionically conductive material according to claim 47, characterized in that the solvent is a solvating polymer, cross-linked or non-cross-linked, which optionally carries grafted ionic groups.

49. Ionically conductive material according to claim 48, characterized in that the solvating polymer is selected from polyethers of linear structure, comb or blocks, which optionally form a network, based on poly(ethylene oxide), copolymers containing the ethylene oxide or propylene oxide or allylglycidylether unit, polyphosphazene, cross-linked networks based on polyethylene glycol cross-linked with isocyanates, networks obtained by polycondensation and carrying groups enabling the incorporation of cross-linkable groups and block copolymers in which at least a fraction of the blocks carry functions which have redox properties.

50. Ionically conductive material according to claim 1, characterized in that the solvent consists essentially of an aprotic liquid solvent and a polar polymer solvent comprising units containing at least one heteroatom selected from sulfur, oxygen, nitrogen and fluorine.

51. Ionically conductive material according to claim 50, characterized in that the polar polymer mainly contains units derived from acrylonitrile, vinylidene fluoride, N-vinylpyrrolidone or methyl methacrylate.

52. Ionically conductive material according to claim 1, characterized in that it additionally contains at least an ionic salt.

53. Ionically conductive material according to claim 1, characterized in that it additionally contains an inorganic or organic charge in the form of powder or fibres.

* * * * *